(12) United States Patent
Childs

(10) Patent No.: US 8,163,790 B2
(45) Date of Patent: Apr. 24, 2012

(54) METRONIDAZOLE COCRYSTALS AND IMIPRAMINE COCRYSTALS

(75) Inventor: Scott Lawrence Childs, Atlanta, GA (US)

(73) Assignee: New Form Pharmaceuticals, Inc., New York, NY (US)

( * ) Notice: Subject to any disclaimer, the term of this patent is extended or adjusted under 35 U.S.C. 154(b) by 541 days.

(21) Appl. No.: 12/096,998

(22) PCT Filed: Dec. 8, 2006

(86) PCT No.: PCT/US2006/046824
§ 371 (c)(1),
(2), (4) Date: Nov. 26, 2008

(87) PCT Pub. No.: WO2007/067727
PCT Pub. Date: Jun. 14, 2007

(65) Prior Publication Data
US 2009/0258859 A1    Oct. 15, 2009

Related U.S. Application Data

(60) Provisional application No. 60/748,202, filed on Dec. 8, 2005.

(51) Int. Cl.
*A61K 31/4164* (2006.01)
*A61K 31/55* (2006.01)
*C07D 233/92* (2006.01)
*C07D 233/18* (2006.01)

(52) U.S. Cl. ............... 514/398; 548/326.5; 540/476; 514/213.01

(58) Field of Classification Search ............... 548/326.5; 540/476; 514/213.01, 398
See application file for complete search history.

(56) References Cited

U.S. PATENT DOCUMENTS 7,452,555 B2 * 11/2008 Childs .................... 424/666
2004/0176335 A1   9/2004 Childs

FOREIGN PATENT DOCUMENTS

| GB | 2 000 025 | 1/1979 |
|---|---|---|
| WO | WO 2004/064762 | 8/2004 |
| WO | WO 2004/078163 | 9/2004 |
| WO | WO 2004/080468 | 9/2004 |

OTHER PUBLICATIONS

International Search Report dated Apr. 3, 2008 (PCT/US2006/046824).
International Preliminary Report on Patentability dated Jun. 25, 2008 (PCT/US2006/046824).
Supplementary European Search Report and Opinion dated Aug. 25, 2010, for EP 06844999.0 (PCT/US2006/046824).
Parfitt (ed.), "Martindale. The complete drug reference. $32^{nd}$ Edition," pp. 289-290 (1999).
O'Neil et al. (ed.), "The Merck Index, $13^{th}$ Edition," p. 883 (2001).
Database Registry, CAS-RN 301812-44-2 (Nov. 9, 2000).
Childs, "Crystal Engineering Approach to Forming Cocrystals of Amine Hydrochlorides with Organic Acids. Molecular Complexes of Fluoxetine Hydrochloride with Benzoic, Succinic, and Fumaric Acids," J. Am. Chem. Soc. 126:13335-13342 (2004).
Etter et al., "The use of cocrystallization as a method of studying hydrogen bond preferences of 2-aminopyridine," J. Chem. Soc., Chem. Commun. 8:589-591 (1990).
Etter et al., "Graph-set analysis of hydrogen-bond patterns in organic crystals," Acta Crystallogr., Sect. B, Struct. Sci. B46:256-262 (1990).
Etter et al., "Hydrogen bond-directed cocrystallization and molecular recognition properties of diarylureas," J. Am. Chem. Soc. 112:8415-8426 (1990).
Görbitz et al., "On the inclusion of solvent molecules in the crystal structures of organic compounds," Acta Cryst. B56:625-534 (2000).
Kumar et al., "Molecular Complexes of Some Mono- and Dicarboxylic Acids with *trans*-1,4-Dithiane-1,4-dioxide," American Chemical Society, Crystal Growth & Design, 2(4):313-318 (2002).
Goodman and Gillman's, "The Pharmacological Basis of Therapeutics"; Tenth Edition, A. Gilman, J. Hardman and L. Limbird, eds., McGraw-Hill Press, pp. 155-173 (2001).
Remington's Pharmaceutical Sciences, Sixteenth Edition E.W. Martin (Mack Publishing Co., Easton, Pa., 1980).
*International Tables for X-ray Crystallography* (A.J.C. Wilson (ed) *International Tables for X-ray Crystallography*, vol. C. Kynoch, Academic Publishers, Dordrecht, 1992, Tables 6.1.1.4 (pp. 500-502) and 4.2.6.8 (pp. 219-222).

* cited by examiner

Primary Examiner — Kamal Saeed
Assistant Examiner — Janet L Coppins
(74) Attorney, Agent, or Firm — J.A. Lindeman & Co., PLLC

(57) ABSTRACT

Cocrystals of metronidazole are described herein. Such cocrystals are a cocrystal of metronidazole with gentisic acid and a cocrystal of metronidazole with gallic acid. Cocrystals of imipramine hydrochloride are also described. Such cocrystals are a cocrystal of imipramine hydrochloride with (+)-camphoric acid, a cocrystal of imipramine hydrochloride with fumaric acid, and a cocrystal of imipramine hydrochloride with 1-hydroxy-2-naphthoic acid.

15 Claims, 24 Drawing Sheets

FIG. 2

```
*** Basic Data Process ***
```

Group Name   : Cocrystals
Data Name    : 140647_01_001
File Name    : 140647_01_001.PKR
Sample Name  : 81899, A16G426_8, Metr
Comment      : 81899, A16G426_8, Metronidazol

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 11 | 26.3998 | 3.37334 | 100 | 0.31480 | 2236 | 20034 |
| 2 | 4  | 14.4515 | 6.12423 | 34  | 0.57960 | 757  | 12520 |
| 3 | 12 | 28.5349 | 3.12560 | 19  | 0.35320 | 425  | 5910  |

Peak Data List

| peak no. | 2Theta (deg) | d (A) | I/I1 | FWHM (deg) | Intensity (Counts) | Integrated Int (Counts) |
|---|---|---|---|---|---|---|
| 1  | 12.0400 | 7.34489 | 10  | 0.51080 | 223  | 5140  |
| 2  | 12.4800 | 7.08691 | 5   | 0.00000 | 119  | 0     |
| 3  | 13.6800 | 6.46783 | 8   | 0.59560 | 186  | 4520  |
| 4  | 14.4515 | 6.12423 | 34  | 0.57960 | 757  | 12520 |
| 5  | 18.9865 | 4.67043 | 11  | 0.56300 | 237  | 4427  |
| 6  | 19.6400 | 4.51647 | 7   | 1.12000 | 148  | 4771  |
| 7  | 21.9125 | 4.05294 | 11  | 0.50110 | 247  | 5874  |
| 8  | 24.2000 | 3.67477 | 6   | 0.00000 | 129  | 0     |
| 9  | 25.1507 | 3.53798 | 19  | 0.37020 | 414  | 5215  |
| 10 | 25.7600 | 3.45566 | 16  | 0.45240 | 368  | 4847  |
| 11 | 26.3998 | 3.37334 | 100 | 0.31480 | 2236 | 20034 |
| 12 | 28.5349 | 3.12560 | 19  | 0.35320 | 425  | 5910  |
| 13 | 29.6447 | 3.01107 | 12  | 0.45350 | 271  | 4435  |
| 14 | 31.2400 | 2.86085 | 8   | 0.42000 | 178  | 3263  |
| 15 | 31.6800 | 2.82211 | 5   | 0.00000 | 120  | 0     |
| 16 | 32.6000 | 2.74454 | 6   | 0.55120 | 140  | 3653  |
| 17 | 32.8800 | 2.72180 | 11  | 0.00000 | 254  | 0     |
| 18 | 33.2000 | 2.69629 | 6   | 1.28000 | 137  | 3051  |
| 19 | 34.3200 | 2.61082 | 5   | 1.09340 | 117  | 4999  |

Xray powder diffraction pattern of a second solid form of gentisic acid (129440.raw).

FIG. 7

```
*** Basic Data Process ***

Group Name   : Cocrystals
Data Name    : 140649_01_001
File Name    : 140649_01_001.PKR
Sample Name  : 83754, A16G423, Metron
Comment      : 83754, A16G423, Metronidazole,
```

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 14 | 25.9186 | 3.43487 | 100 | 0.45750 | 1153 | 17068 |
| 2 | 1  | 12.4289 | 7.11593 | 79  | 0.43870 | 912  | 13958 |
| 3 | 17 | 28.0321 | 3.18051 | 35  | 0.62430 | 399  | 9554  |

Peak Data List

| peak no. | 2Theta (deg) | d (A) | I/I1 | FWHM (deg) | Intensity (Counts) | Integrated Int (Counts) |
|---|---|---|---|---|---|---|
| 1  | 12.4289 | 7.11593 | 79  | 0.43870 | 912  | 13958 |
| 2  | 13.9200 | 6.35685 | 10  | 0.00000 | 114  | 0 |
| 3  | 14.6400 | 6.04580 | 12  | 0.00000 | 135  | 0 |
| 4  | 15.2419 | 5.80838 | 26  | 0.55250 | 303  | 5569 |
| 5  | 15.8800 | 5.57639 | 11  | 0.00000 | 131  | 0 |
| 6  | 17.6400 | 5.02378 | 12  | 1.36000 | 137  | 5482 |
| 7  | 18.0800 | 4.90250 | 8   | 0.00000 | 95   | 0 |
| 8  | 18.6000 | 4.76660 | 9   | 0.00000 | 106  | 0 |
| 9  | 19.6436 | 4.51565 | 22  | 0.57270 | 254  | 6812 |
| 10 | 22.0000 | 4.03702 | 9   | 0.00000 | 100  | 0 |
| 11 | 22.5200 | 3.94497 | 13  | 0.00000 | 149  | 0 |
| 12 | 23.3600 | 3.80498 | 11  | 0.00000 | 130  | 0 |
| 13 | 25.0400 | 3.55337 | 19  | 1.02000 | 222  | 8199 |
| 14 | 25.9186 | 3.43487 | 100 | 0.45750 | 1153 | 17068 |
| 15 | 27.0400 | 3.29491 | 16  | 0.00000 | 187  | 0 |
| 16 | 27.3200 | 3.26177 | 16  | 0.00000 | 189  | 0 |
| 17 | 28.0321 | 3.18051 | 35  | 0.62430 | 399  | 9554 |
| 18 | 29.4000 | 3.03557 | 11  | 0.00000 | 126  | 0 |
| 19 | 29.9600 | 2.98009 | 10  | 0.00000 | 117  | 0 |
| 20 | 30.6400 | 2.91549 | 12  | 0.00000 | 135  | 0 |
| 21 | 31.1600 | 2.86801 | 8   | 0.00000 | 95   | 0 |
| 22 | 33.2800 | 2.69000 | 9   | 0.00000 | 106  | 0 |
| 23 | 33.9200 | 2.64069 | 8   | 4.32000 | 95   | 6350 |

Xray powder diffraction pattern of a solid form of (+)-camphoric acid acid (106067_09_B10.raw).

Xray powder diffraction pattern of a third solid form of (+)-camphoric acid acid (109790_D10_19_raw).

FIG. 14

```
         *  Basic Data Process  *

Group Name   : Cocrystals
Data Name    : 140650_01_001
File Name    : 140650_01_001.PKR
Sample Name  : 8375S, A24G479, Imipra
Comment      : 8375S, A24G479, Imipramine HCl

# Strongest 3 peaks
  no.  peak   2Theta       d       I/I1    FWHM     Intensity    Integrated Int
        no.   (deg)       (A)               (deg)    (Counts)      (Counts)
   1    16   18.2261    4.86353    100    0.44780      419           6081
   2    27   25.5838    3.47906     82    0.44020      342           4833
   3     8   13.6679    6.47353     75    0.45070      315           4430

# Peak Data List
       peak   2Theta       d       I/I1    FWHM     Intensity    Integrated Int
        no.   (deg)       (A)               (deg)    (Counts)      (Counts)
         1    5.3605    16.47273    38    0.59530      161           5740
         2    6.9200    12.76352    18    0.00000       75              0
         3    8.7200    10.13247    28    0.00000      117              0
         4    9.0800     9.73153    43    0.48800      180           3082
         5   10.7116     8.25260    48    0.49670      201           3520
         6   11.8057     7.49013    37    0.62860      156           3824
         7   12.9600     6.82549    21    0.00000       86              0
         8   13.6679     6.47353    75    0.45070      315           4430
         9   14.4800     6.11224    58    0.59420      245           3143
        10   15.0400     5.88589    69    0.56720      289           3888
        11   15.4000     5.74910    58    0.00000      242              0
        12   15.6400     5.66141    53    0.00000      224              0
        13   16.1997     5.46705    59    0.62600      249           4540
        14   16.6800     5.31069    24    0.00000       99              0
        15   17.5258     5.05626    68    0.43690      283           4098
        16   18.2261     4.86353   100    0.44780      419           6081
        17   18.8000     4.71634    56    0.00000      234              0
        18   19.1200     4.63812    50    0.41720      208           3759
        19   19.8800     4.46249    23    0.00000       95              0
        20   20.5256     4.32356    68    0.62160      287           4885
        21   21.0400     4.21900    26    0.00000      109              0
        22   21.6000     4.11087    23    0.00000       98              0
        23   22.2784     3.98720    43    0.54540      180           4130
        24   23.1600     3.83738    28    0.00000      116              0
        25   23.7200     3.74804    52    0.38940      219           2317
        26   24.0800     3.69281    43    0.81460      179           3441
        27   25.5838     3.47906    82    0.44020      342           4833
        28   26.1200     3.40884    34    0.00000      141              0
        29   26.4000     3.37332    33    0.00000      137              0
        30   27.0000     3.29970    33    0.00000      140              0
        31   27.4800     3.24315    21    0.00000       87              0
        32   28.0400     3.17963    25    0.00000      104              0
        33   28.8400     3.09323    30    0.00000      125              0
        34   29.1600     3.06001    27    0.00000      114              0
        35   29.8800     2.98789    24    0.00000       99              0
        36   30.2000     2.95695    29    0.00000      121              0
        37   30.5600     2.92294    24    0.00000      102              0
        38   31.0820     2.87503    40    0.51600      167           3176
        39   31.8000     2.81173    20    0.00000       82              0
        40   32.4400     2.75771    28    0.00000      118              0
        41   33.0000     2.71218    18    0.00000       75              0
        42   33.6000     2.66510    26    0.86000      107           4206
```

FIG. 17

```
*** Basic Data Process ***

Group Name  : Cocrystals
Data Name   : 140652_01_001
File Name   : 140652_01_001.PKR
Sample Name : 83756, A24G41, Imipram
Comment     : 83756, A24G41, Imipramine HCl,
```

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 3  | 13.9818 | 6.32889 | 100 | 0.36740 | 744 | 8305 |
| 2 | 15 | 25.0737 | 3.54867 | 76  | 0.51330 | 563 | 8622 |
| 3 | 9  | 19.5847 | 4.52910 | 42  | 0.45270 | 309 | 3967 |

Peak Data List

| peak no. | 2Theta (deg) | d (A) | I/I1 | FWHM (deg) | Intensity (Counts) | Integrated Int (Counts) |
|---|---|---|---|---|---|---|
| 1  | 8.7133  | 10.14024 | 18  | 1.05330 | 134 | 9595 |
| 2  | 12.7264 | 6.95024  | 27  | 0.55440 | 200 | 4872 |
| 3  | 13.9818 | 6.32889  | 100 | 0.36740 | 744 | 8305 |
| 4  | 15.2545 | 5.80361  | 41  | 0.41570 | 302 | 3550 |
| 5  | 15.8800 | 5.57639  | 18  | 0.56000 | 137 | 2501 |
| 6  | 17.1600 | 5.16321  | 19  | 0.56000 | 143 | 2017 |
| 7  | 17.5500 | 5.04934  | 31  | 0.46000 | 228 | 2174 |
| 8  | 18.8400 | 4.70641  | 14  | 0.93340 | 103 | 2613 |
| 9  | 19.5847 | 4.52910  | 42  | 0.45270 | 309 | 3967 |
| 10 | 20.8916 | 4.24863  | 38  | 0.38450 | 283 | 4206 |
| 11 | 21.6000 | 4.11087  | 15  | 0.00000 | 114 | 0 |
| 12 | 22.3600 | 3.97283  | 15  | 0.00000 | 110 | 0 |
| 13 | 23.2000 | 3.83085  | 25  | 0.42000 | 185 | 2711 |
| 14 | 23.4800 | 3.78580  | 37  | 0.42860 | 273 | 2881 |
| 15 | 25.0737 | 3.54867  | 76  | 0.51330 | 563 | 8622 |
| 16 | 25.7200 | 3.46094  | 14  | 0.00000 | 101 | 0 |
| 17 | 26.4800 | 3.36331  | 18  | 0.00000 | 133 | 0 |
| 18 | 26.8000 | 3.32387  | 28  | 0.48000 | 210 | 2866 |
| 19 | 27.7102 | 3.21672  | 22  | 0.40540 | 167 | 2557 |
| 20 | 28.2800 | 3.15319  | 13  | 0.00000 | 99  | 0 |
| 21 | 28.8000 | 3.09743  | 22  | 0.46220 | 166 | 2645 |
| 22 | 29.7600 | 2.99966  | 21  | 0.38280 | 158 | 2484 |
| 23 | 30.2000 | 2.95695  | 16  | 0.00000 | 117 | 0 |
| 24 | 30.6400 | 2.91549  | 13  | 0.00000 | 93  | 0 |
| 25 | 31.3600 | 2.85017  | 14  | 0.00000 | 106 | 0 |
| 26 | 31.9600 | 2.79802  | 12  | 0.76000 | 90  | 2188 |
| 27 | 33.5800 | 2.66665  | 10  | 1.24000 | 75  | 4318 |

FIG. 20

```
               *  Basic Data Process  *

Group Name   : Cocrystals
Data Name    : 140653_01_001
File Name    : 140653_01_001.PKR
Sample Name  : 83757, A24G409, Imipra
Comment      : 83757, A24G409, Imipramine HCl
```

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 10 | 18.1541 | 4.88265 | 100 | 0.36620 | 566 | 5040 |
| 2 | 21 | 26.8292 | 3.32032 | 97 | 0.37490 | 550 | 6121 |
| 3 | 18 | 24.1773 | 3.67817 | 72 | 0.38130 | 407 | 5000 |

Peak Data List

| peak no. | 2Theta (deg) | d (A) | I/I1 | FWHM (deg) | Intensity (Counts) | Integrated Int (Counts) |
|---|---|---|---|---|---|---|
| 1 | 8.1051 | 10.89974 | 31 | 0.54170 | 177 | 5114 |
| 2 | 10.0523 | 8.79234 | 46 | 0.48190 | 262 | 5424 |
| 3 | 11.1200 | 7.95041 | 19 | 0.00000 | 106 | 0 |
| 4 | 12.9600 | 6.82549 | 20 | 0.00000 | 113 | 0 |
| 5 | 14.1634 | 6.24815 | 57 | 0.40460 | 323 | 4674 |
| 6 | 15.0800 | 5.87037 | 29 | 0.55340 | 166 | 2035 |
| 7 | 15.4400 | 5.73430 | 33 | 0.43700 | 188 | 1806 |
| 8 | 16.2400 | 5.45357 | 21 | 0.56000 | 118 | 2315 |
| 9 | 17.6800 | 5.01250 | 38 | 0.42360 | 214 | 3122 |
| 10 | 18.1541 | 4.88265 | 100 | 0.36620 | 566 | 5040 |
| 11 | 18.9804 | 4.67191 | 58 | 0.45130 | 331 | 4547 |
| 12 | 20.2800 | 4.37536 | 69 | 0.53200 | 389 | 5643 |
| 13 | 20.9200 | 4.24293 | 67 | 0.36080 | 380 | 3832 |
| 14 | 21.6171 | 4.10766 | 32 | 0.47430 | 180 | 2313 |
| 15 | 22.3718 | 3.97076 | 42 | 0.44910 | 238 | 2854 |
| 16 | 23.3200 | 3.81141 | 31 | 0.44920 | 177 | 2966 |
| 17 | 23.8000 | 3.73562 | 26 | 0.00000 | 149 | 0 |
| 18 | 24.1773 | 3.67817 | 72 | 0.38130 | 407 | 5000 |
| 19 | 25.3981 | 3.50407 | 65 | 0.33440 | 369 | 5344 |
| 20 | 26.1600 | 3.40372 | 26 | 0.00000 | 147 | 0 |
| 21 | 26.8292 | 3.32032 | 97 | 0.37490 | 550 | 6121 |
| 22 | 27.5200 | 3.23852 | 33 | 0.50280 | 188 | 3842 |
| 23 | 28.5200 | 3.12720 | 15 | 0.00000 | 85 | 0 |
| 24 | 28.8400 | 3.09323 | 21 | 0.00000 | 117 | 0 |
| 25 | 29.2400 | 3.05182 | 15 | 0.00000 | 86 | 0 |
| 26 | 29.9600 | 2.98009 | 17 | 0.58660 | 98 | 1670 |
| 27 | 30.3600 | 2.94173 | 24 | 0.71460 | 136 | 2867 |
| 28 | 34.2533 | 2.61575 | 17 | 1.52000 | 99 | 7342 |

METRONIDAZOLE COCRYSTALS AND IMIPRAMINE COCRYSTALS

This application claims priority under 35 U.S.C. §119(e) to U.S. Provisional Application No. 60/748,202, filed Dec. 8, 2005, herein incorporated by reference in its entirety.

Cocrystals are crystals that contain two or more non-identical molecules. Examples of cocrystals may be found in the Cambridge Structural Database. Examples of cocrystals may also be found at Etter, Margaret C., and Daniel A. Adsmond (1990) "The use of cocrystallization as a method of studying hydrogen bond preferences of 2-aminopyridine" *J. Chem. Soc., Chem. Commun.* 1990 589-591, Etter, Margaret C., John C. MacDonald, and Joel Bernstein (1990) "Graph-set analysis of hydrogen-bond patterns in organic crystals" *Acta Crystallogr., Sect. B, Struct. Sci.* B46 256-262, Etter, Margaret C., Zofia Urbańczyk-Lipkowska, Mohammad Zia-Ebrahimi, and Thomas W. Panunto (1990b) "Hydrogen bond directed cocrystallization and molecular recognition properties of diarylureas" *J. Am. Chem. Soc.* 112 8415-8426, which are incorporated herein by reference in their entireties. The following articles are also incorporated herein by reference in their entireties: Carl Henrik Görbotz and Hans-Petter Hersleth, 2000, "On the inclusion of solvent molecules in the crystal structures of organic compounds"; Acta Cryst. (2000), B56, 625-534; and V. S. Senthil Kumar, Ashwini Nangia, Amy K. Katz and H. L. Carrell, 2002, "Molecular Complexes of Some Mono- and Dicarboxylic Acids with trans-1,4,-Dithiane-1,4-dioxide" American Chemical Society, Crystal Growth & Design, Vol. 2, No. 4, 2002.

By cocrystallizing an active agent with a guest, one creates new a solid form which has unique properties compared with existing solid forms of that active agent. For example, a cocrystal may have different dissolution and solubility properties than the active agent itself or as a salt. An active agent is a molecule that has a desired activity. In the pharmaceutical field, the active agent is often a known as an active pharmaceutical ingredient ("API"), and the other component of the cocrystal (the guest) is often a pharmaceutically acceptable compound (which could also be an API). Cocrystals containing APIs can be used to deliver APIs therapeutically. New drug formulations comprising cocrystals of APIs with pharmaceutically acceptable guests may have superior properties over existing drug formulations. Active agents and guests may also include nutraceuticals, agricultural chemicals, pigments, dyes, explosives, polymer additives, lubricant additives, photographic chemicals, and structural and electronic materials.

As used herein, solid forms include, but are not limited to, polymorphs, allotropes, clathrates, solvates, salts, cocrystals, semicrystalline, and amorphous forms of a compound or cocrystal.

When the active agent, such as an API, is a hydrochloride (HCl) salt, for example, one can cocrystallize the HCl salt with a neutral guest molecule. By doing this one can create a cocrystal with specific properties. For instance one can make a cocrystal comprising an active pharmaceutical ingredient having greater or lesser intrinsic solubility and/or a faster or slower dissolution rate, depending on the guest compound that is chosen.

Intrinsic dissolution is the dissolution rate of a drug substance under the condition of constant surface area and is used to compare dissolution properties of different drug substances or different solid forms of the same drug substance. Solid forms with different intrinsic dissolution rates can be used to make drug products with different properties. For example, a solid form with a rapid intrinsic dissolution rate could be used to make an immediate release formulation. By comparison, a solid form with a slow dissolution rate could be used to make a sustained release drug formulation. Thus, the dissolution rate of a cocrystal, when compared with that of the API alone or as a salt, can be used as measure of whether a drug formulation with a faster or slower release profile could be made, and, therefore, can be used to prepare a beneficial pharmaceutical product.

By "guest" what is meant is the component of the cocrystal that is not the active agent of the cocrystal. The guest is present in order to form the cocrystal with the active agent. Thus, the guest is part of the crystal lattice. It is contemplated that one or more guests may be employed in a cocrystal, according to any of the techniques of the disclosure. Accordingly, the guest is not required to have an activity of its own, although it may have some activity. In some situations, the guest may have the same activity as or an activity complementary to that of the active agent. The guest may be another active agent. For example, some guests may facilitate the therapeutic effect of an active pharmaceutical ingredient. For pharmaceutical formulations, the guest may be any pharmaceutically acceptable molecule that forms a cocrystal with the API or its salt. The Registry of Toxic Effects of Chemical Substances (RTECS) database is a useful source for toxicology information, and the GRAS list contains about 2500 relevant compounds. Both sources may be used to help identify guests.

The guest may be neutral (or non-ionized), such as benzoic acid and succinic acid, or ionic, such as sodium benzoate or sodium succinate. Neutral guests are non-ionized guests. Ionic guests are compounds or complexes having ionic bonds. General classes of guests include but are not limited to organic bases, organic salts, alcohols, aldehydes, amino acids, sugars, ionic inorganics, aliphatic esters, aliphatic ketones, organic acids, aromatic esters, and aromatic ketones.

Typically, guests will have the ability to form complementary non-covalent interactions with the active agent or its salt, including APIs and salts thereof, for example the ability to form hydrogen bonds with the active agent or its salt. Guests for active agents, such as APIs, having negative counterions include, but are not limited to, compounds having alcohol, ketone, ester, and/or carboxylic acid functionalities. Guests may include organic acids, organic bases, organic salts, alcohols, aldehydes, amino acids, sugars, ionic inorganic compounds, aliphatic esters and ketones, and aromatic esters and ketones. Specific examples of carboxylic acid guests are found in table 1.

TABLE 1

| | |
|---|---|
| L-(+)-tartaric acid | glycolic acid |
| citric acid | 1-hydroxy-2-naphthoic acid |
| benzoic acid | gentisic acid |
| fumaric acid | DL-tartaric acid |
| adipic acid | maleic acid |
| succinic acid | oxalic acid |
| L-malic acid | gallic acid |
| 4-hydroxybenzoic acid | hippuric acid |
| glutaric acid | (+)-camphoric acid |
| DL-malic acid | pyroglutamic acid |
| malonic acid | ketoglutaric acid. |
| salicylic acid | |

Properties of active agents or their salts, such as APIs or salts thereof, may be modified by forming a cocrystal. Such properties include melting point, density, hygroscopicity, crystal morphology, loading volume, compressibility, and shelf life. Furthermore, other properties such as bioavailability, dissolution, solubility, toxicity, taste, physical stability, chemical stability, production costs, and manufacturing method may be modified by using a cocrystal rather than the API alone, or as a salt.

An active agent, such as an API, can be screened for possible cocrystals where polymorphic forms, hydrates, or solvates do not readily form. For example, a neutral compound that can only be isolated as amorphous material could be cocrystallized. Forming a cocrystal may upgrade the performance of a drug formulation of an API by, for example, changing one or more properties identified earlier. A cocrystal may also be used to isolate or purify a compound during manufacturing. If it is desirable to identify all of the solid state phases of an active pharmaceutical ingredient, then cocrystallization may be particularly desirable.

Those of ordinary skill in the pharmaceutical arts use analytical techniques to characterize crystals, including cocrystals. For example, the chemical identity of the components of cocrystals can often be determined with solution-state techniques such as $^{13}C$ or $^1H$ NMR. While it may help identify the active agent, such as an API, and the guest, such solution-state techniques, however, do not provide information about the cocrystal solid-state structure. There are, however, solid-state analytical techniques that can be used to provide information about solid-state structure including single crystal x-ray diffraction, powder x-ray diffraction, solid state $^{13}C$ NMR, Raman spectroscopy, and thermal techniques. Neither x-ray powder diffraction nor Raman spectroscopy themselves give direct data on the stoichiometry of the components that make up a cocrystal. There are techniques, however, that do provide such information. For example, single crystal x-ray diffraction provides this information because it gives a three-dimensional map of the atoms and bonds in the unit cell thus directly providing the stoichiometry within the cocrystal and gives the precise stoichiometry within the unit cell. In addition, solution-state techniques such as NMR may be used to confirm the molar ratios of component species.

Single-crystal x-ray diffraction provides three-dimensional structural information about the positions of atoms and bonds in a crystal. It is not always possible or feasible, however, to obtain such a structure from a crystal, such as a cocrystal, due to, for example, insufficient crystal size or difficulty in preparing crystals of sufficient quality for single-crystal x-ray diffraction. Structural identification information can, however, be obtained from other solid-state techniques such as x-ray powder diffraction and Raman spectroscopy. These techniques are used to generate data on a solid crystal, such as a cocrystal. Once that data has been collected on a known cocrystal, that data can be used to identify the presence of that cocrystal in other materials. Thus, these data characterize the cocrystal. For example, one may use an x-ray powder diffraction pattern, or a portion thereof, to serve as a fingerprint which characterizes a cocrystal and differentiates the cocrystal from its component API and guest thereby showing that the cocrystal is indeed a new material and not a physical mixture of API and guest. A cocrystal will exhibit a different x-ray powder diffraction pattern, and a different Raman spectrum, than its components or a linear combination thereof.

In x-ray powder diffraction, an x-ray source directs x-rays onto a sample where the x-rays are diffracted by the electrons associated with the atoms in the sample. The diffracted x-rays are collected by a detector and provide a pattern that may be used as a fingerprint for a crystalline solid. Thus, crystals of the same structure provide the same x-ray powder diffraction pattern.

An x-ray powder diffraction plot is an x-y graph with °2θ (diffraction) on the x-axis and intensity on the y-axis. The peaks within this plot may be used to characterize a cocrystal. Although the peaks within an entire diffractogram may be used to characterize a cocrystal, one may rely on a subset of that data to characterize a cocrystal. The data is often represented by the position of the peaks on the x-axis rather than the intensity of peaks on the y-axis because peak intensity may vary with sample orientation. There is also variability in the position of peaks on the x-axis. There are several sources of this variability. One comes from sample preparation. Samples of the same crystalline material, such as a cocrystal, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same cocrystal. Likewise, different software packages process x-ray data differently and this also leads to variability. These and other sources of variability are known to those of ordinary skill in the pharmaceutical arts. Due to these sources of variability, it is common to recite x-ray diffraction peaks using the word "about" prior to the peak value in °2θ. The word "about" incorporates this variability which under most sampling conditions and most data collection and data processing conditions leads to a variability in peak position of about plus or minus 0.2 °2θ. Thus, when a peak is said to be at about 10.5 °2θ, then under most sampling, data collection, and data processing conditions, that peak will appear between 10.3 °2θ and 10.7 °2θ. In characterizing the cocrystal of this invention, the x-ray diffraction peaks were all measured using Cu-Kα1 radiation and all peaks herein cited refer to peaks diffracted from x-rays with that wavelength. Thus, when characterizing a cocrystal, those of ordinary skill in the art will select a peak or set of peaks from the x-ray powder diffraction pattern of the cocrystal wherein at least one of those peaks is at least 0.4 °2θ from any of the peaks in the x-ray powder diffraction patterns of the component active agents and guests of the cocrystal.

Raman spectroscopy is another technique that may be used to characterize cocrystals together with or separately from x-ray powder diffraction. Raman spectroscopy is a scattering technique wherein a light source, often a laser, is used to interact with a sample. Raman scattered light, which is light that interacts with the sample, is collected by a detector and the intensity of that light can be plotted versus the "wavenumber" of the light to obtain a spectrum. A wavenumber has the units of inverse centimeters ($cm^{-1}$). Wavenumbers are plotted on the x-axis of a Raman spectrum with intensity on the y-axis. As with x-ray powder diffraction plots, Raman peaks are recorded by reference to their wavenumber position rather than their intensity. Variation in the position of Raman peaks also exists and may be due to sample conditions as well as data collection and processing. The typical variation of Raman spectra is on the order plus or minus 2.0 wavenumbers. Thus, a cocrystal with a peak at "about" 780.5 $cm^{-1}$ means that under most conditions in most instruments that cocrystal will exhibit a peak between about 778.5 $cm^{-1}$ and about 782.5 $cm^{-1}$.

BRIEF DESCRIPTION OF THE DRAWINGS

FIG. 2 is an x-ray powder diffraction peak list of peaks in FIG. 1.

FIG. 7 is an x-ray powder diffraction peak list of peaks in FIG. 6.

FIG. 14 is an x-ray powder diffraction peak list of peaks in FIG. 9.

FIG. 17 is an x-ray powder diffraction peak list of peaks in FIG. 16.

FIG. 20 is an x-ray powder diffraction peak list of peaks in FIG. 19.

DETAILED DESCRIPTION

Cocrystals of Metronidazole and Cocrystals of Imipramine Hydrochloride

The present invention is directed to cocrystals of metronidazole and cocrystals of imipramine hydrochloride. Metronidazole cocrystals and imipramine hydrochloride cocrystals of the present invention are crystals in that they are an orderly arrangement of molecules or atoms in a solid with the smallest repeatable three-dimensional building block being termed "the unit cell."

Metronidazole is an FDA-approved drug used for the treatment of bacterial infections. Specifically, metronidazole has activity against anaerobic gram-negative bacilli, including the *Bacteroides fragilis* group and *Fusobacterium*. It also has activity against anaerobic gram-positive bacilli including *Clostridium* species and susceptible strains of *Eubacterium* and is also used as a treatment against anaerobic gram-positive cocci including *Peptococcus niger* and *Peptostreptococcus*. The chemical structure of metronidazole appears below:

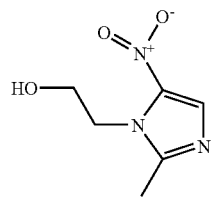

Two cocrystals of metronidazole are disclosed herein. The first is a cocrystal of metronidazole and gentisic acid and the second is a cocrystal of metronidazole and gallic acid. Dissolution studies of the metronidazole:gallic acid cocrystal are described below.

Imipramine hydrochloride is an FDA-approved drug for the treatment of depression. It is in the class of drugs known as tricyclic antidepressants and its chemical structure appears below:

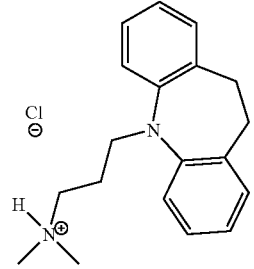

Three cocrystals of imipramine are further disclosed herein. The first is a cocrystal of imipramine hydrochloride and (+) camphoric acid. The second is a cocrystal of imipramine hydrochloride and fumaric acid. The third is a cocrystal of imipramine hydrochloride and 1-hydroxy-2-naphthoic acid. Dissolution studies were performed on both the fumaric acid cocrystal and the 1-hyroxy-2-naphthoic acid cocrystal.

Metronidazole:Gentisic Acid Cocrystal

One cocrystal of the invention is a cocrystal of metronidazole and gentisic acid. Single-crystal x-ray diffraction has shown the stoichiometry of metronidazole to gentisic acid to be 1:1 in the unit cell. Both x-ray powder diffraction data and Raman spectral data were collected on this cocrystal.

Figure 1:
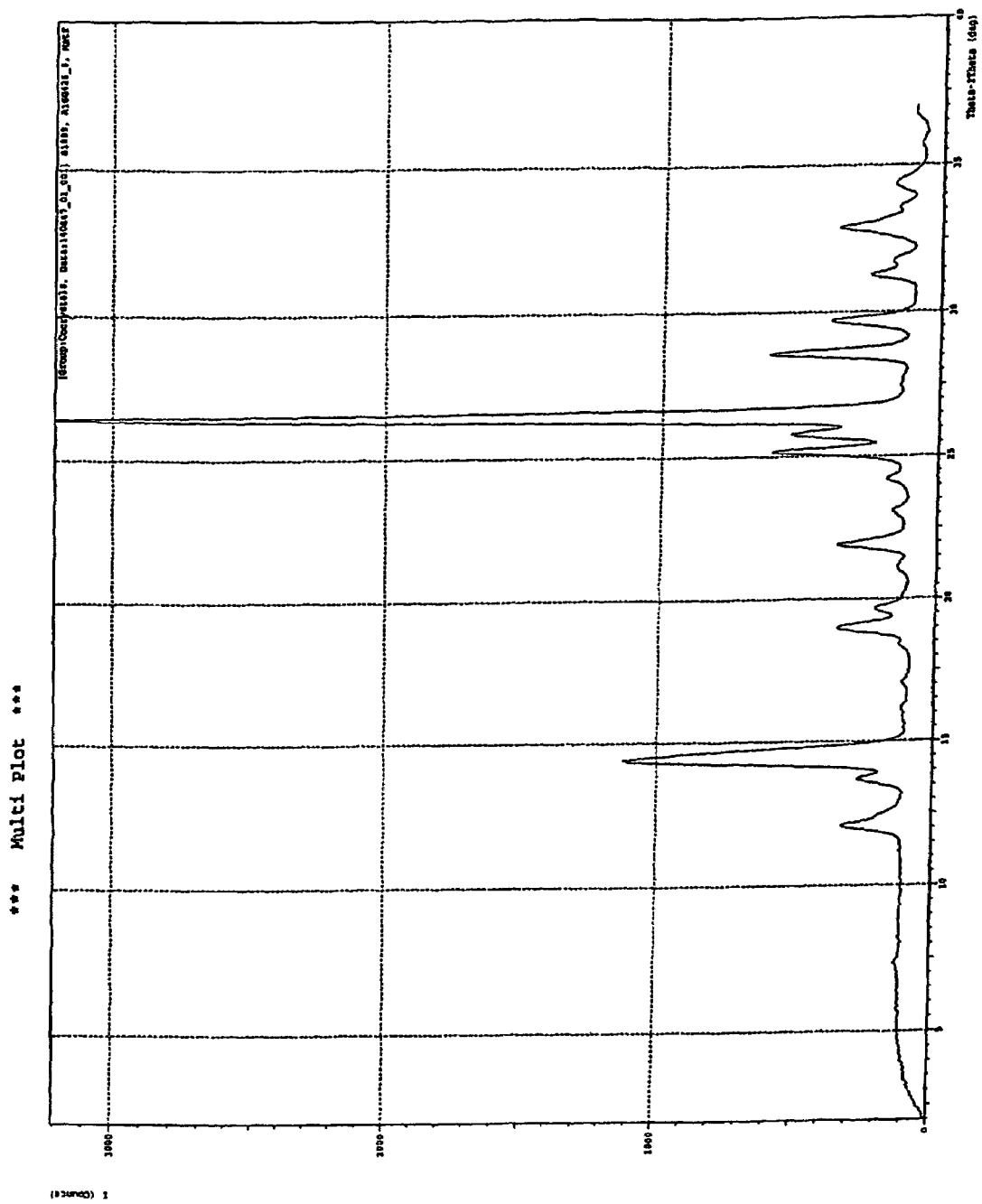
FIG. 1 is an x-ray powder diffraction pattern of a cocrystal of metronidazole with gentisic acid.
Figure 3:
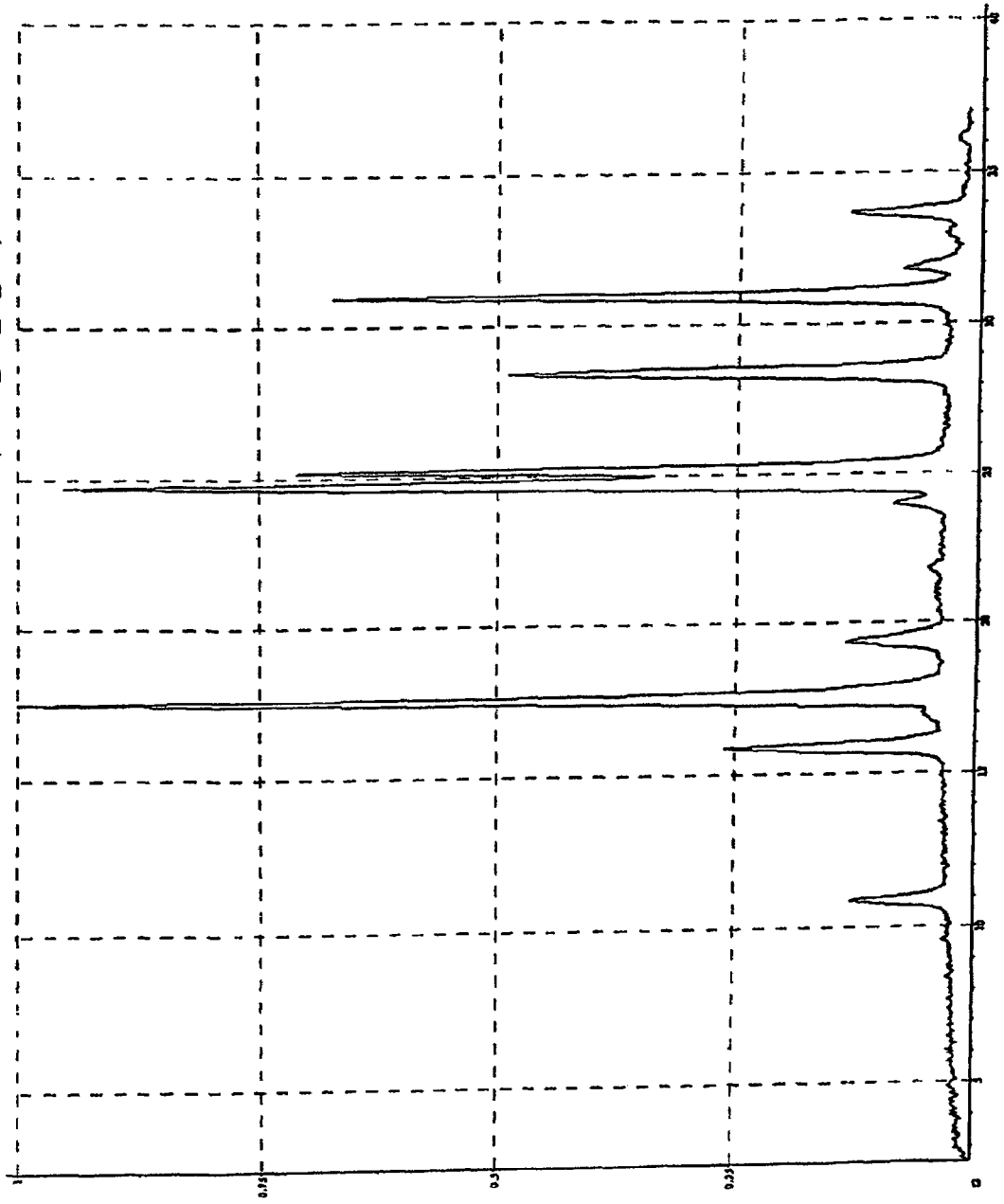
FIG. 3 is an x-ray diffraction pattern of a solid form of gentisic acid.
Figure 4:
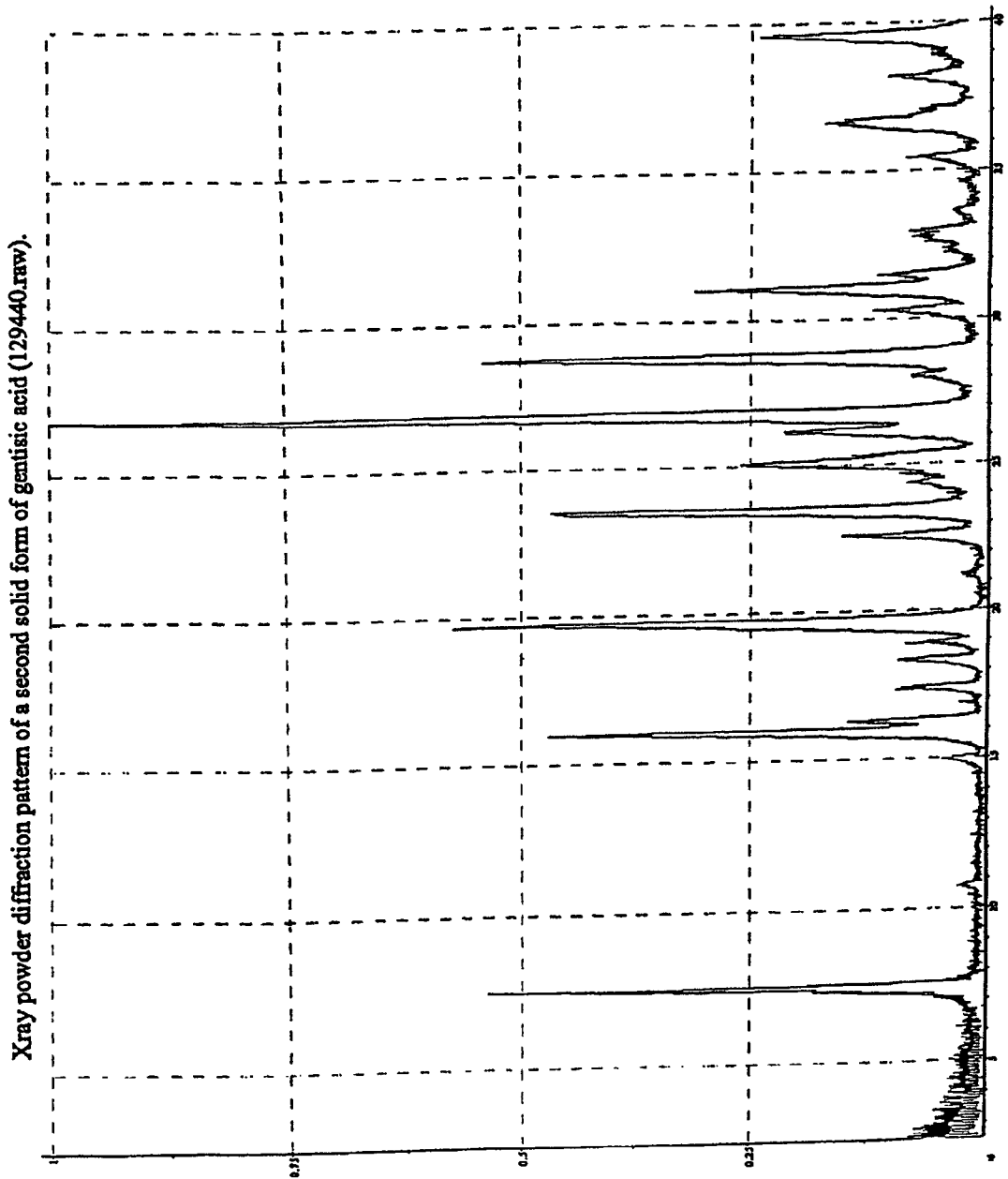
FIG. 4 is an x-ray diffraction pattern of a second solid form of gentisic acid.

FIG. 1 is a powder diffraction pattern of the metronidazole:gentisic acid cocrystal. FIG. 2 is the corresponding peak table for the diffractogram in FIG. 1. While the diffractogram of FIG. 1 could be used to characterize the cocrystal, it may also be characterized with a subset of that data. For example, the peak at about 14.5 °2θ in FIG. 2, which has been rounded from 14.4515 °2θ to the nearest 0.1 degree two theta, is more than 0.4 °2θ away from any peak in the x-ray powder diffraction pattern of metronidazole. In addition, the x-ray diffraction patterns of the known forms of gentisic acid in the ICDD PFD-4 database (International Centre for Diffraction Data, 12 Campus Boulevard, Newtown Square, Pa. 19073-3273 U.S.A.) as well as from diffraction patterns of gentisic acid collected internally (see FIG. 2A) show that no gentisic acid peak occurs within 0.4 °2θ of 14.5 °2θ. Thus, the peak at 14.5 °2θ characterizes the metronidazole:gentisic acid cocrystal. Likewise, no peak in metronidazole or any of the gentisic acid diffraction patterns appear within 0.4 °2θ of 25.8 °2θ, which is a peak in the metronidazole:gentisic acid cocrystal in FIG. 2 and has been rounded from 25.7600 °2θ to the nearest 0.1 degree two-theta. Thus, the peak at 25.8 °2θ is another peak that alone or together with the peak at 14.5 °2θ characterizes the metronidazole:gentisic acid cocrystal.

Figure 5:
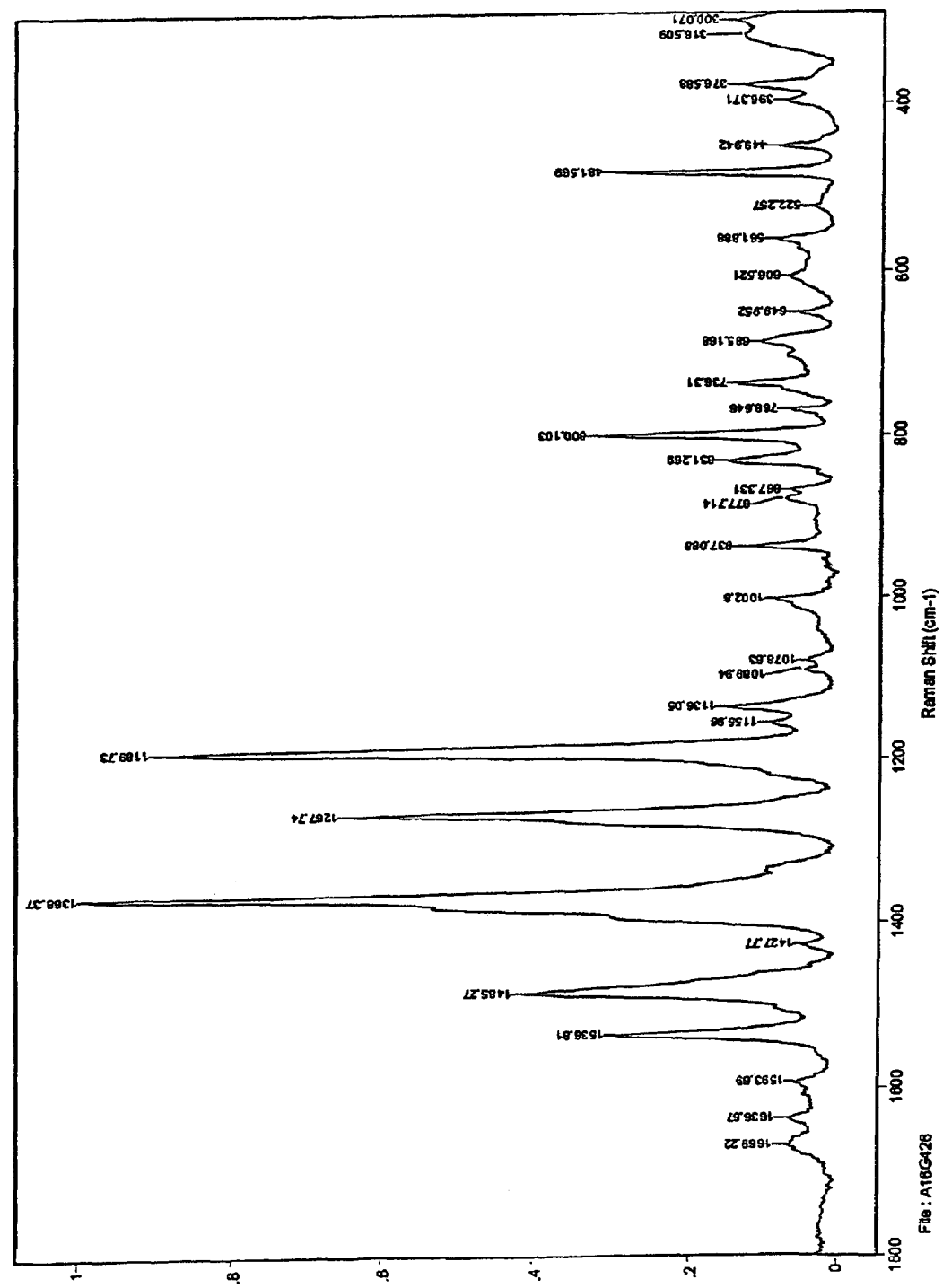
FIG. 5 is a Raman spectrum of a cocrystal of metronidazole with gentisic acid.

FIG. 5 is a peak picked Raman spectrum of the cocrystal of metronidazole and gentisic acid. While the entire Raman spectrum of FIG. 5 could be used to characterize the cocrystal of metronidazole and gentisic acid, it is not necessary to use the entire spectrum. A subset of the spectrum may be used to characterize the cocrystal of metronidazole and gentisic acid. For example, the peak at about 1189.7 cm$^{-1}$ is more than 4.0 cm$^{-1}$ away from Raman peaks in metronidazole or gentisic acid alone. Thus, the peak at about 1189.7 cm$^{-1}$ may be used to characterize the cocrystal of metronidazole and gentisic acid. Likewise, peaks at about 1368.4 cm$^{-1}$ and about 937.1 cm$^{-1}$ are each more than 4.0 cm$^{-1}$ away from Raman peaks in metronidazole and gentisic acid respectively. Raman spectra from metronidazole and gentisic acid for comparison were collected on the starting materials prior to cocrystallization. Thus, the peaks at about 1368.4 cm$^{-1}$ and about 937.1 cm$^{-1}$ may alone, together, or in combination with the peak at about 1198.7 cm$^{-1}$ be used to characterize the metronidazole:gentisic acid cocrystal. The Raman data reported from FIG. 5 were all rounded to the nearest 0.1 cm$^{-1}$.

One may also use a combination of x-ray diffraction and Raman peaks to characterize a cocrystal. For example, any combination of the three Raman peaks at about 1368.4cm$^{-1}$, about 937.1 cm$^{-1}$, or about 1198.7 cm$^{-1}$ may be used with any of the two x-ray peaks at about 14.5 °2θ and about 25.8 °2θ to characterize the metronidazole:gentisic acid cocrystal.

Metronidazole:Gallic Acid Cocrystal

Figure 6:
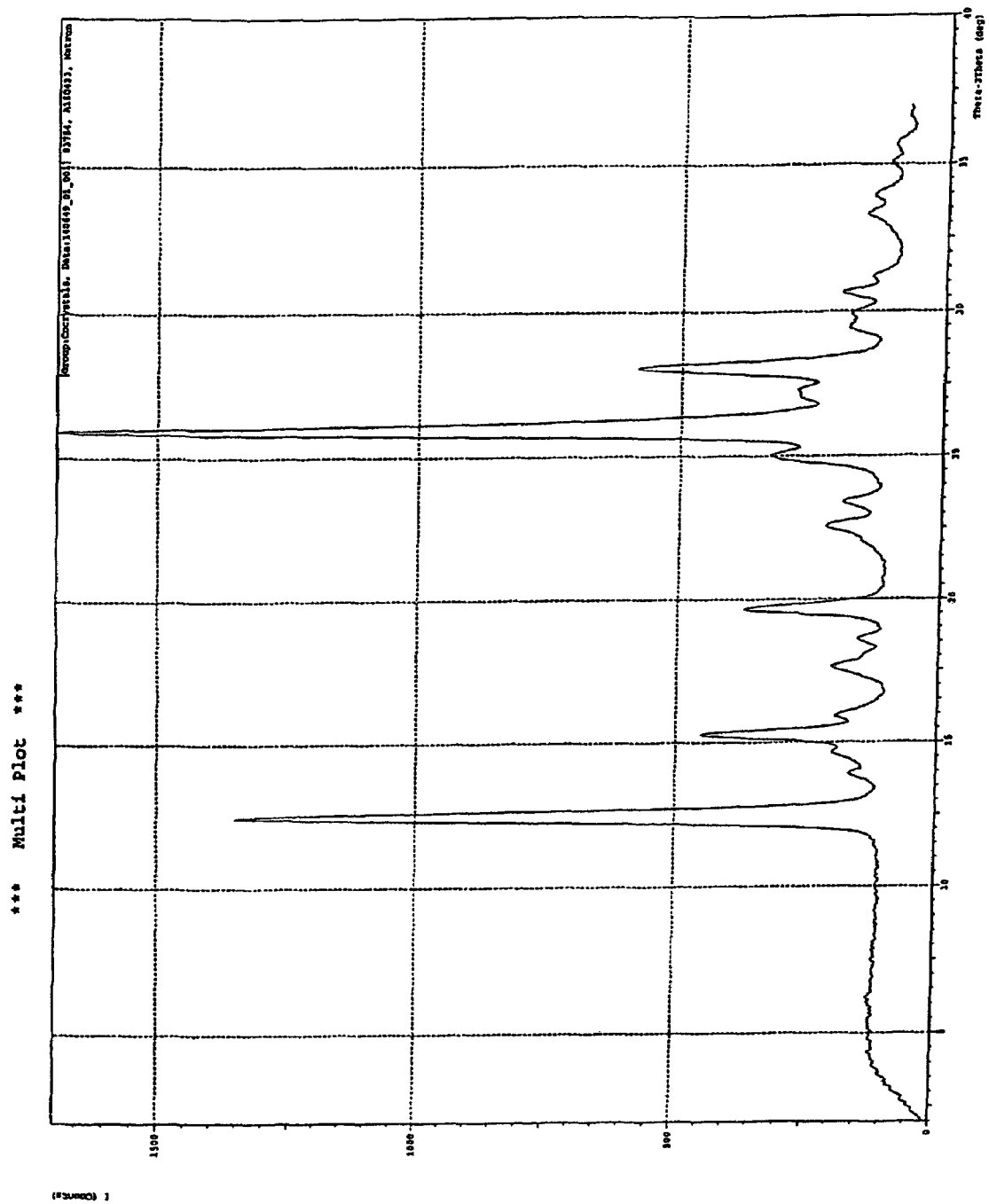
FIG. 6 is an x-ray diffraction pattern of a cocrystal of metronidazole with gallic acid.

Another cocrystal of the invention is a cocrystal of metronidazole and gallic acid. The Scale-up experiments in examples 3 and 4 using a known molar ratio of host and guest confirmed a stoichiometry of 1:1 for metronidazole to gallic acid. FIG. 6 is the x-ray diffraction pattern of the cocrystal of metronidazole and gallic acid. FIG. 7 is the corresponding peak table for the diffractogram in FIG. 6. While the diffractogram of FIG. 6 could be used to characterize the cocrystal, it may also be characterized with a subset of that data. For example, the peak at about 15.2 °2θ in FIG. 6 is more than 0.4 °2θ away from any peak in the x-ray powder diffraction pattern of metronidazole. In addition, the x-ray diffraction patterns of known forms of gallic acid in the ICDD PFD-4 database (International Centre for Diffraction Data, 12 Campus Boulevard, Newtown Square, Pa. 19073-3273 U.S.A.) show that no gallic acid peak occurs within 0.4 °2θ of 15.2 °2θ. No additional forms of gallic acid were found other than the ones from the ICDD PFD-4 database. Thus, the peak at about 15.2 °2θ may be used to characterize the metronidazole:gallic acid cocrystal. Likewise, no peak in metronidazole or any of the gallic acid diffraction patterns appear within 0.4 °2θ of 22.5 °2θ, which is a peak in the metronidazole:gallic acid cocrystal. Thus, the peak at 22.5 °2θ is another peak that alone or together with the peak at 15.2 °2θ characterizes the metronidazole:gallic acid cocrystal.

Figure 8:
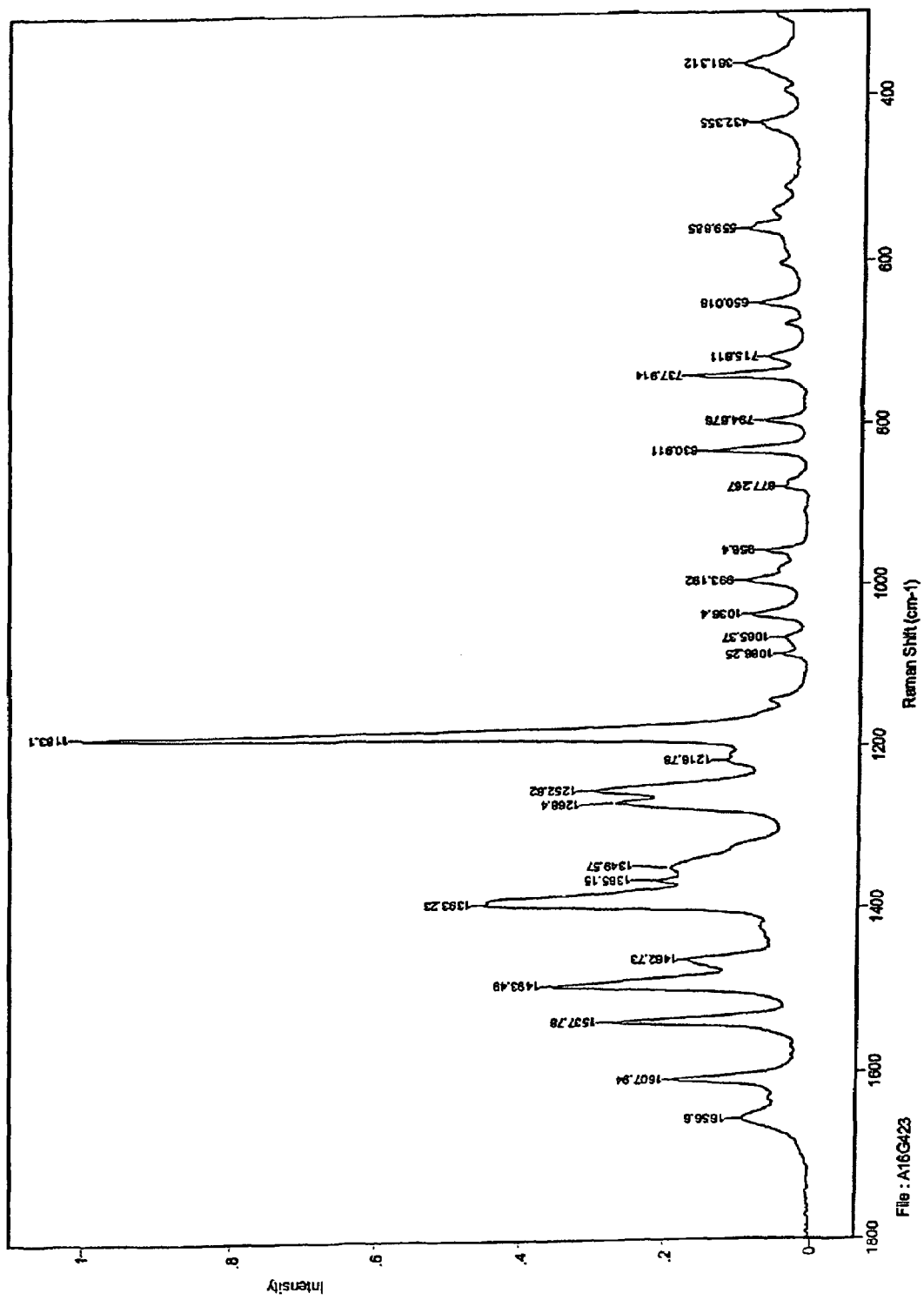
FIG. 8 is a Raman spectrum of a cocrystal of metronidazole and gallic acid.

FIG. 8 is a peak picked Raman spectrum of the cocrystal of metronidazole and gallic acid. While the entire Raman spectrum of FIG. 8 could be used to characterize the cocrystal of metronidazole and gallic acid, it is not necessary to use the entire spectrum. A subset of the spectrum may be used to characterize the cocrystal of metronidazole and gallic acid. For example, the peak at about 1537.8 cm$^{-1}$ is more than 4.0 cm$^{-1}$ away from Raman peaks in metronidazole or gallic acid alone. Thus, the peak at about 1537.8 cm$^{-1}$ may be used to characterize the cocrystal of metronidazole and gallic acid. Likewise, peaks at about 1493.5 cm$^{-1}$ and about 1036.4 cm$^{-1}$ are each more than 4.0 cm$^{-1}$ away from Raman peaks in metronidazole and gallic acid respectively. Raman spectra from metronidazole and gallic acid for comparison were collected on the starting materials prior to cocrystallization. Thus, the peaks at about 1493.5 cm$^{-1}$ and about 1036.4 cm$^{-1}$ may alone, together, or in combination with the peak at about 1198.7 cm$^{-1}$ be used to characterize the metronidazole:gallic acid cocrystal. The Raman data reported from FIG. 8 were all rounded to the nearest 0.1 cm$^{-1}$.

One may also use a combination of x-ray diffraction and Raman peaks to characterize a cocrystal. For example, any combination of the three Raman peaks at about 1537.8 cm$^{-1}$, about 1493.5 cm$^{-1}$, or about 1036.4 cm$^{-1}$ may be used with any of the two x-ray peaks at about 15.2 °2θ and about 22.5 °2θ to characterize the metronidazole:gallic acid cocrystal.

A dissolution study on the metronidazole:gallic acid cocrystal indicated that the cocrystal dissolved at a rate of about 22% of metronidazole. This difference in dissolution rate may be used to develop a drug product comprising a cocrystal of metronidazole:gallic acid to delivers a slower release dose profile of metronidazole than metronidazole as currently used.

Imipramine Hydrochloride:(+)-Camphoric Acid Cocrystal

Figure 9:
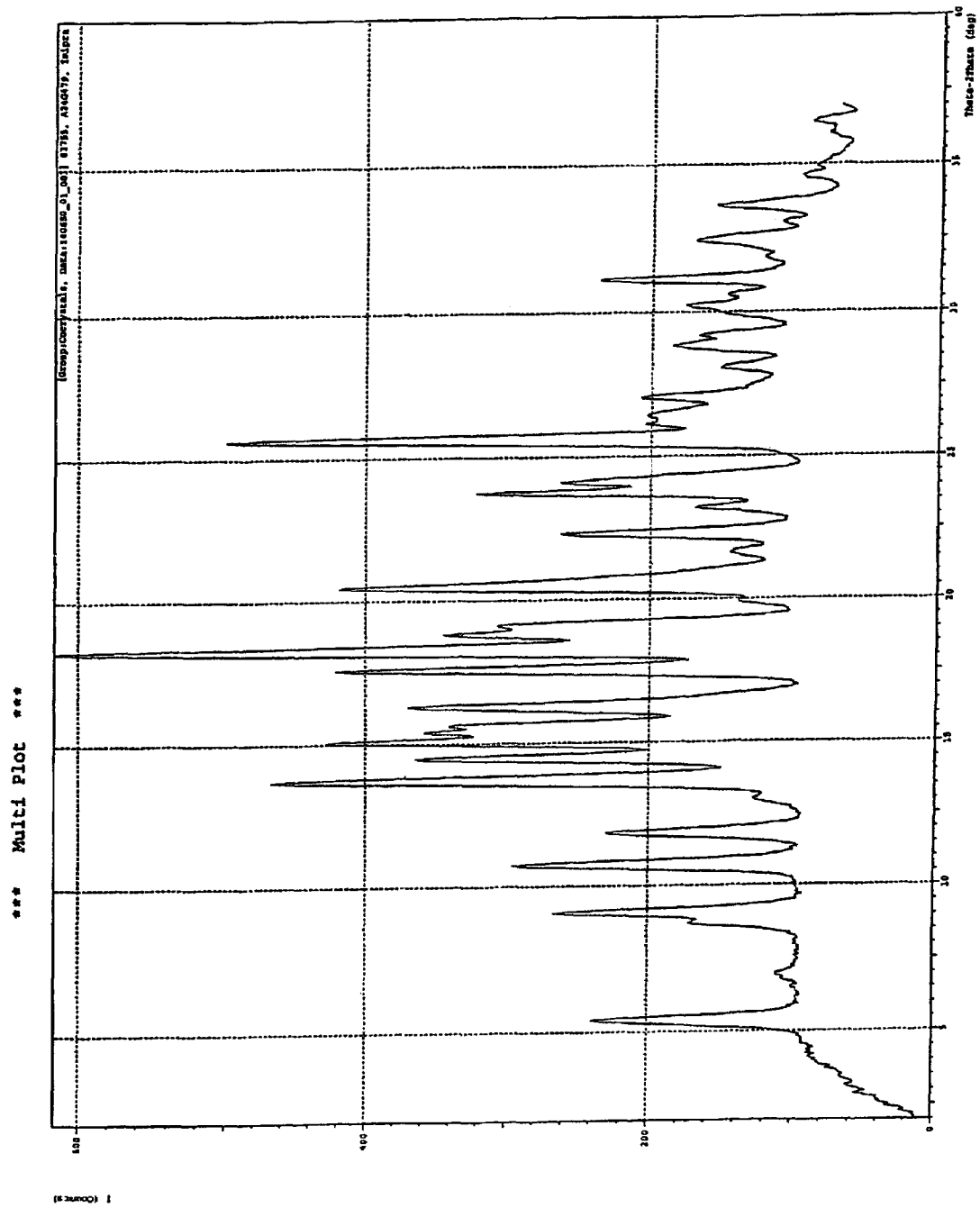
FIG. 9 is an x-ray powder diffraction pattern of a cocrystal of imipramine hydrochloride and (+)-camphoric acid.
Figure 10:
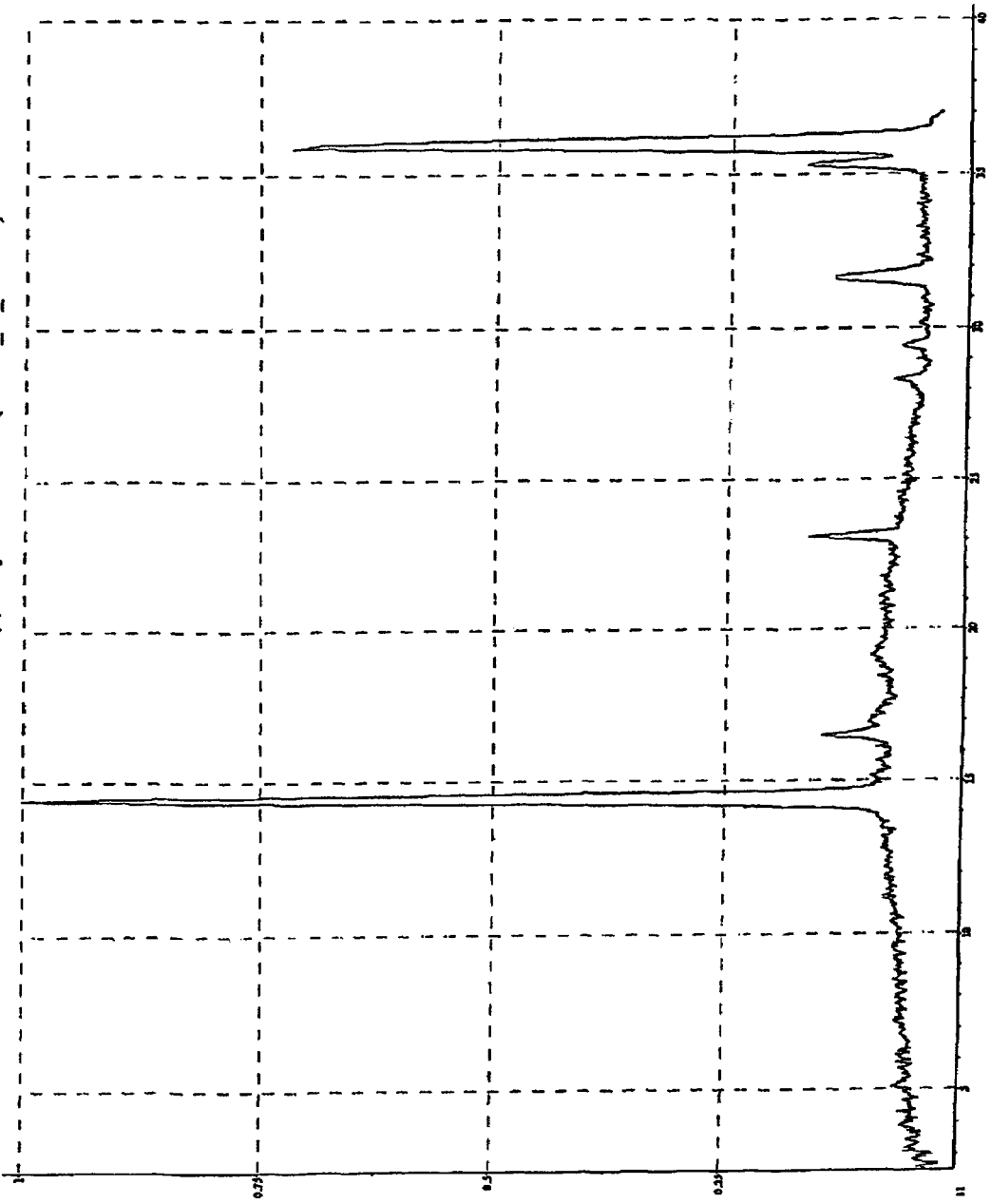
FIG. 10 is an x-ray diffraction pattern of a solid form of (+)-camphoric acid.
Figure 11:
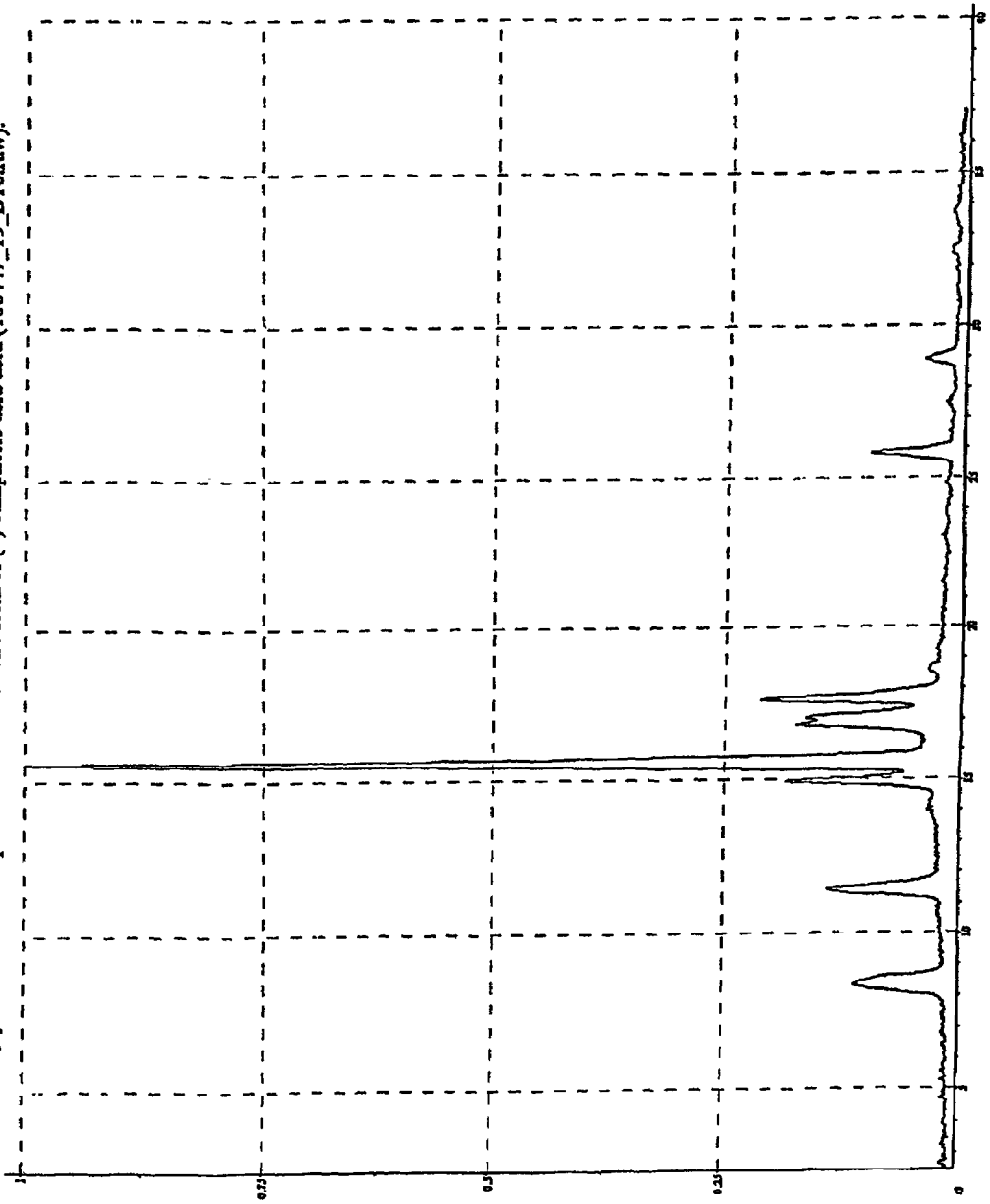
FIG. 11 is an x-ray diffraction pattern of a second solid form of (+)-camphoric acid.
Figure 12:
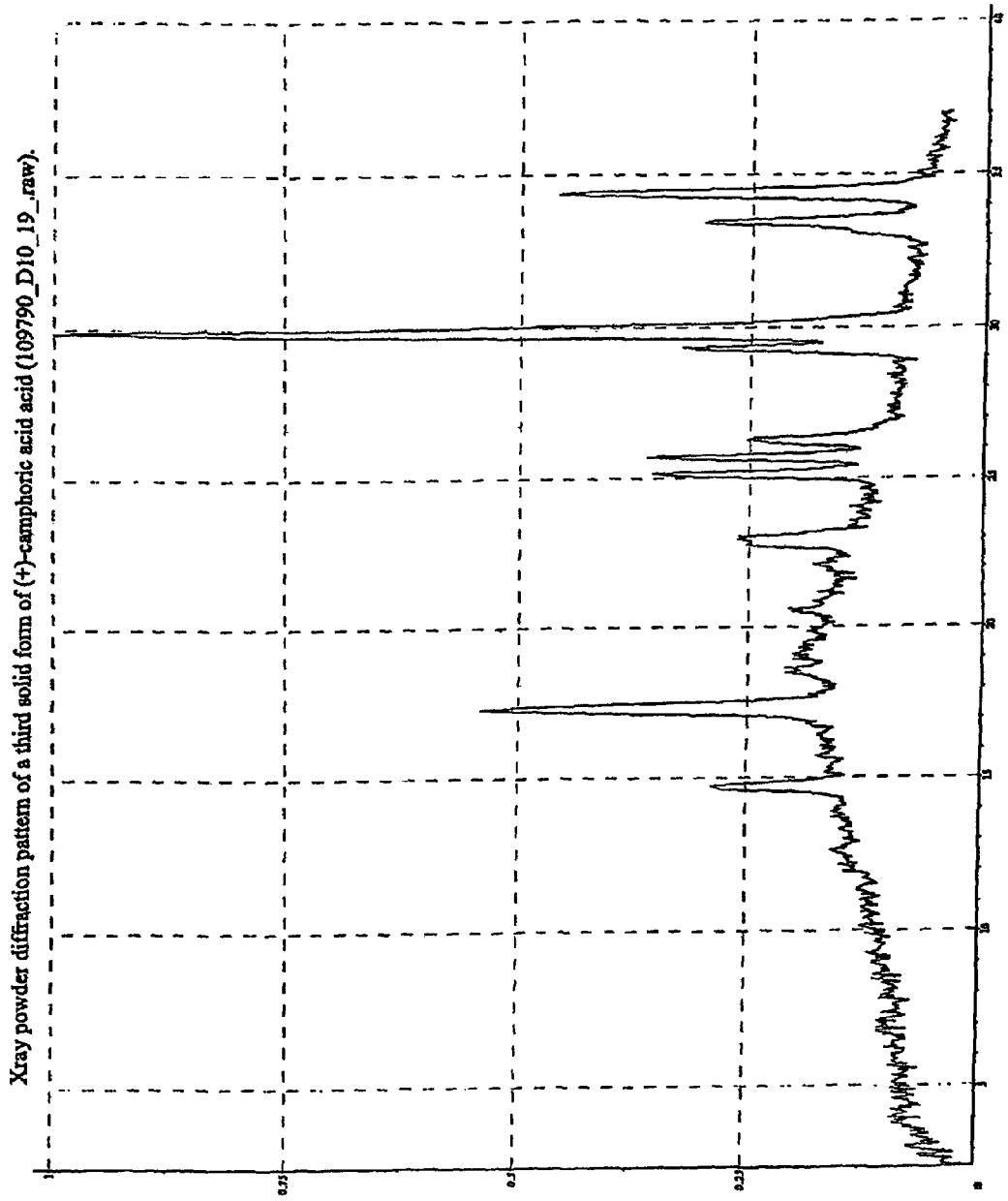
FIG. 12 is an x-ray diffraction pattern of a third solid form of (+)-camphoric acid.
Figure 13:
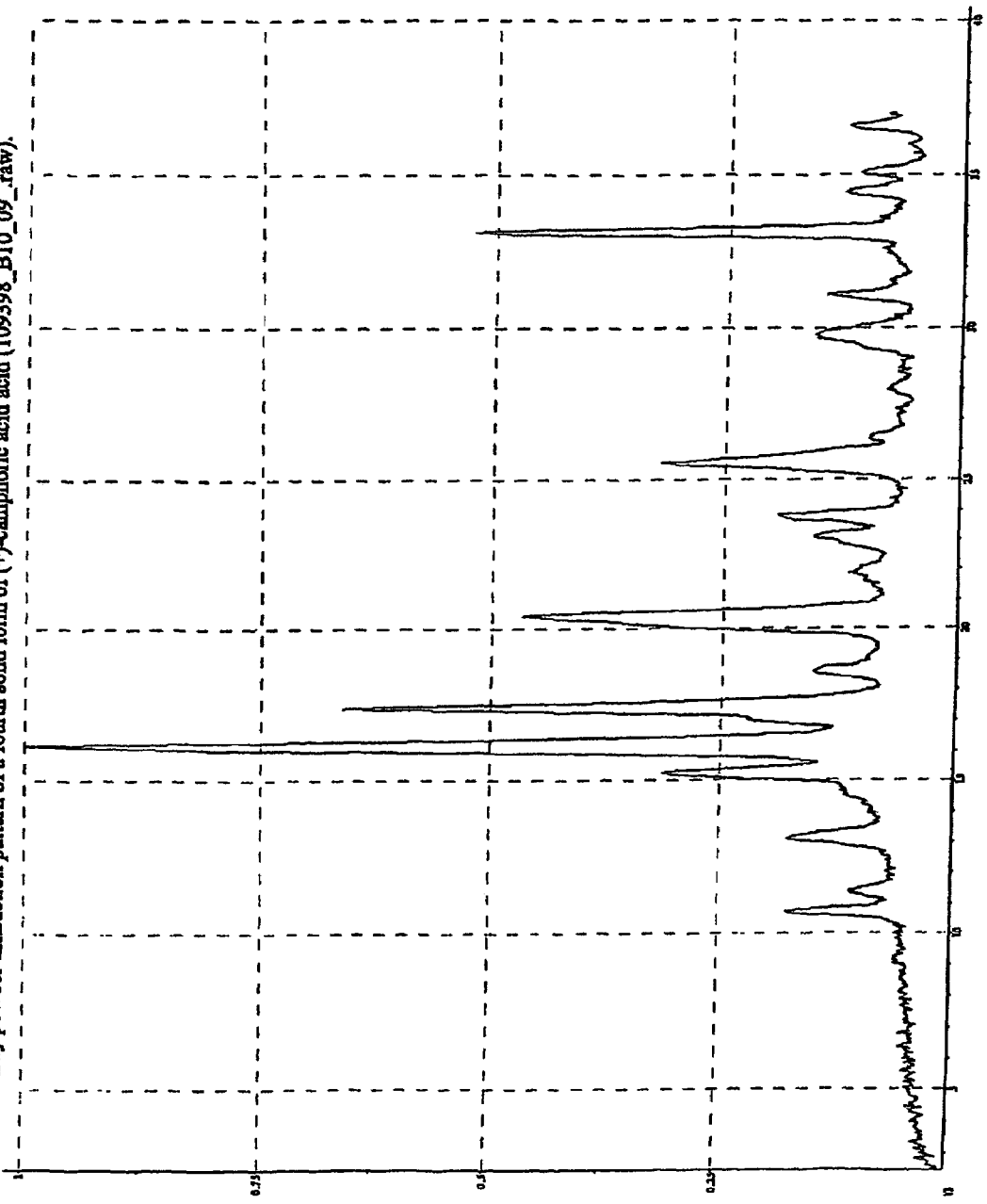
FIG. 13 is an x-ray diffraction pattern of a fourth solid form of (+)-camphoric acid.

Another cocrystal of the invention is a cocrystal of imipramine hydrochloride with (+) camphoric acid. FIG. 9 is a powder diffraction pattern of the imipramine hydrochloride:(+)-camphoric acid cocrystal. FIG. 14 is the corresponding peak table for the diffractogram in FIG. 9. While the diffractogram of FIG. 9 could be used to characterize the cocrystal, it may also be characterized with a subset of that data. For example, the peak at about 5.4 °2θ in FIG. 10, which has been rounded to the nearest 0.1 degree two theta from the value of 5.3605 °2θ reported in FIG. 9, is more than 0.4 °2θ away from any peak in the x-ray powder diffraction pattern of imipramine hydrochloride. In addition, the x-ray diffraction patterns of known forms of (+)-camphoric acid in the ICDD PFD-4 database (International Centre for Diffraction Data, 12 Campus Boulevard, Newtown Square, Pa. 19073-3273 U.S.A.) as well as from diffraction patterns of (+)-camphoric acid collected internally (see FIG. 10) show that no (+)-camphoric acid peak occurs within 0.4 °2θ of 5.4 °2θ. Thus, the peak at about 5.4 °2θ characterizes the imipramine hydrochloride acid:(+)-camphoric acid cocrystal.

Figure 15:
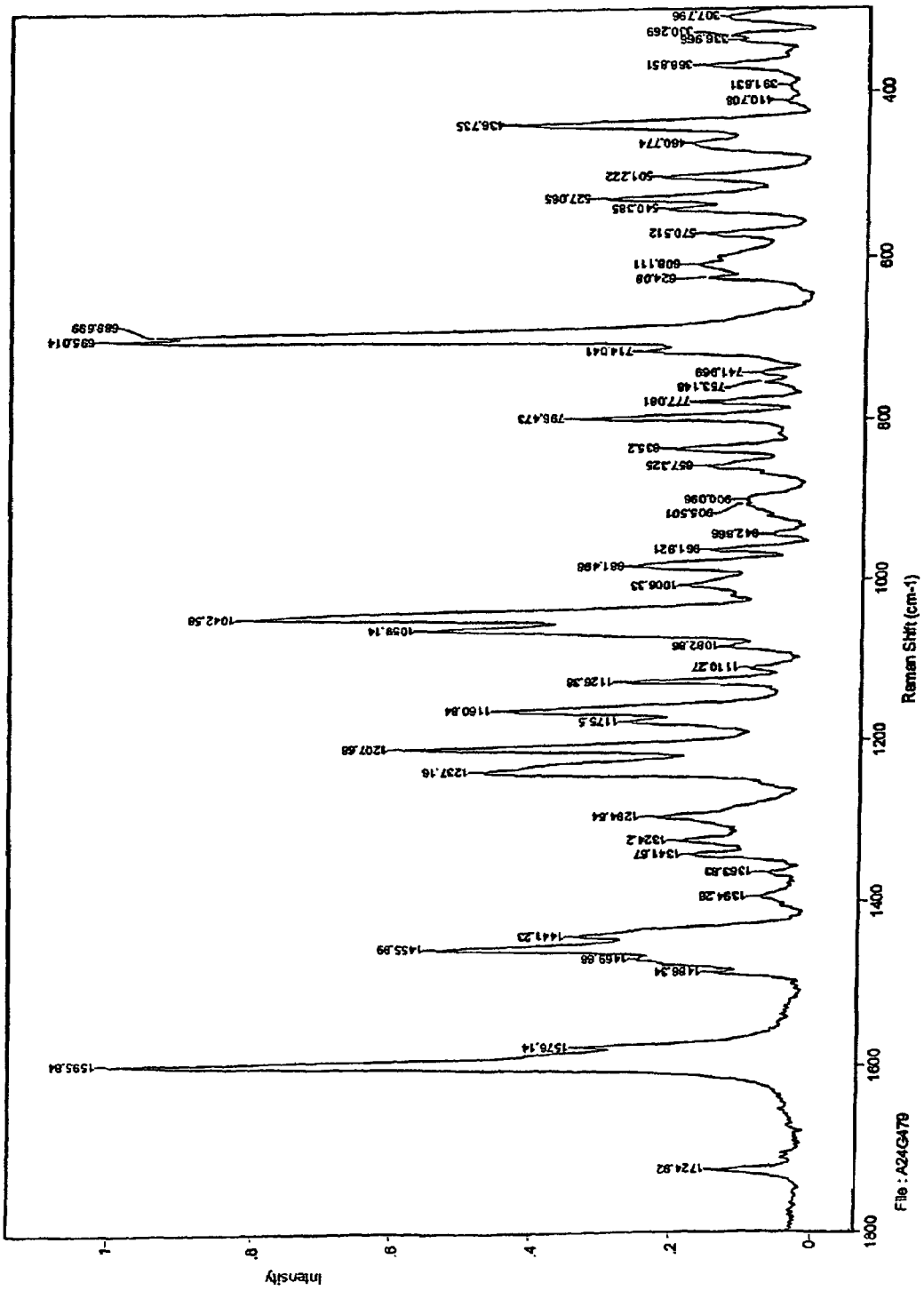
FIG. 15 is a Raman spectrum of a cocrystal of imipramine hydrochloride and (+)-camphoric acid.

FIG. 15 is a peak picked Raman spectrum of the cocrystal of imipramine hydrochloride and (+)-camphoric acid. While the entire Raman spectrum of FIG. 15 could be used to characterize the cocrystal of imipramine hydrochloride and (+)-camphoric acid, it is not necessary to use the entire spectrum. A subset of the spectrum may be used to characterize the cocrystal of imipramine hydrochloride and (+)-camphoric acid. For example, the peak at about 1059.1 cm$^{-1}$ is more than 4.0 cm$^{-1}$ away from Raman peaks in imipramine hydrochloride or (+)-camphoric acid alone. Thus, the peak at about 1059.1 cm$^{-1}$ be used to characterize the cocrystal of imipramine hydrochloride and (+)-camphoric acid. Likewise, peaks at about 1324.2 cm$^{-1}$ and about 527.1 cm$^{-1}$ are each more than 4.0 cm$^{-1}$ away from Raman peaks in imipramine hydrochloride and (+) camphoric acid respectively. Raman spectra from imipramine hydrochloride and (+)-camphoric acid for comparison were collected on the starting materials prior to cocrystallization. Thus, the peaks at about 1324.2 cm$^{-1}$ and about 527.1 cm$^{-1}$ may alone, together, or in combination with the peak at about 1059.1 cm$^{-1}$ be used to characterize the imipramine hydrochloride:(+)-camphoric acid cocrystal. The Raman data reported from FIG. 15 were all rounded to the nearest 0.1 cm$^{-1}$.

One may also use a combination of x-ray diffraction and Raman peaks to characterize a cocrystal. For example, any combination of the three Raman peaks at about 1059.1 cm$^{-1}$, about 1324.2 cm$^{-1}$, or about 527.1 cm$^{-1}$ may be used with the x-ray peak at about 5.4 °2θ to characterize the imipramine hydrochloride:(+) camphoric acid cocrystal.

Imipramine Hydrochloride:Fumaric Acid Cocrystal

Another cocrystal of the invention is a cocrystal of imipramine hydrochloride with fumaric acid. A single crystal x-ray showed the ratio of imipramine hydrochloride to fumaric acid to be 2:1 in the unit cell.

Figure 16:
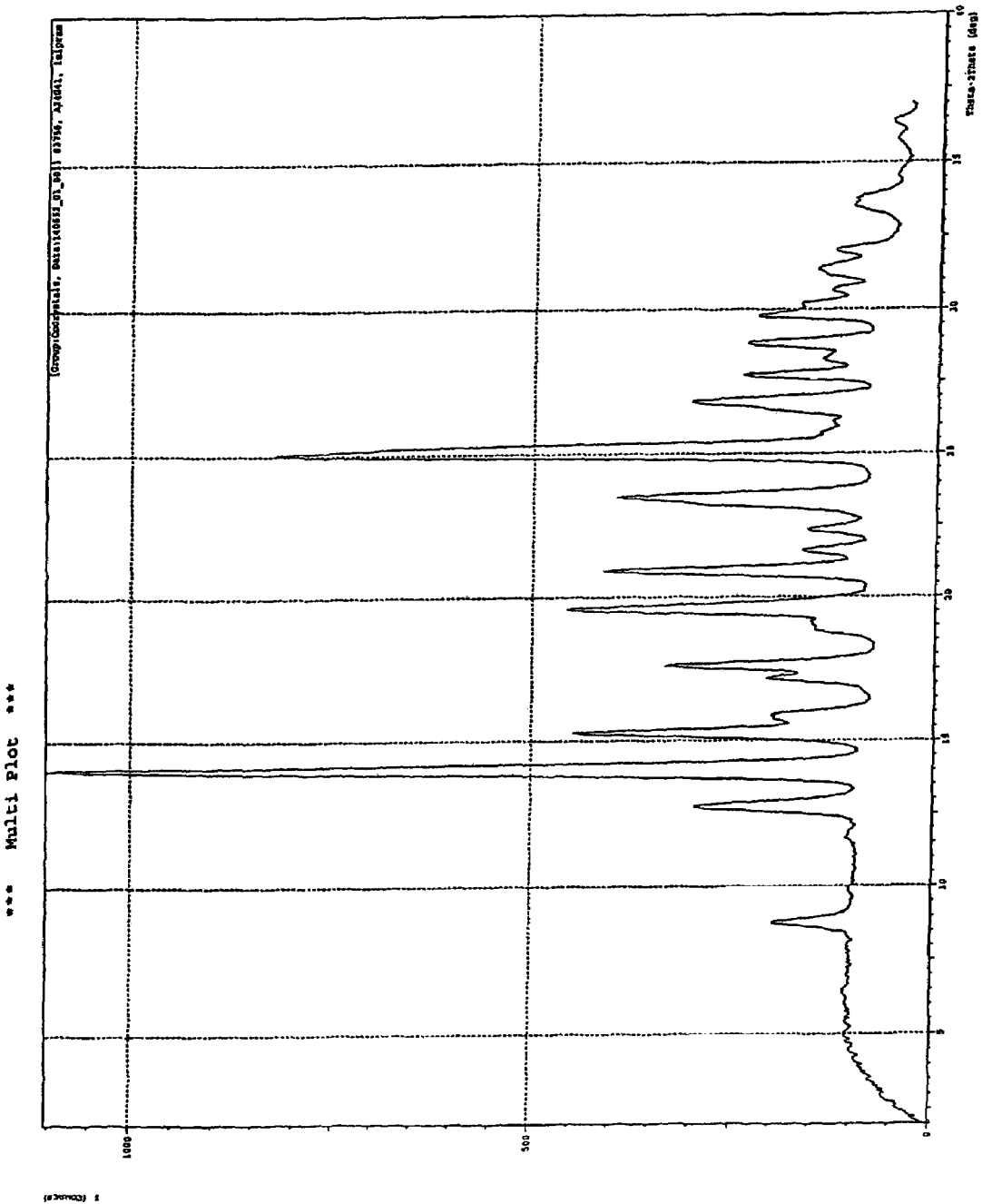
FIG. 16 is an x-ray powder diffraction pattern of imipramine hydrochloride and fumaric acid.

FIG. 16 is a powder diffraction pattern of the imipramine hydrochloride:fumaric acid cocrystal. FIG. 17 is the corresponding peak table for the diffractogram in FIG. 16. While the diffractogram of FIG. 16 could be used to characterize the cocrystal, it may also be characterized with a subset of that data. For example, the peak at about 14.0 °2θ in FIG. 17, which was reported as 13.9818 °2θ in FIG. 17 but has been rounded to the nearest 0.1 °2θ, is more than 0.4 °2θ away from any peak in the x-ray powder diffraction pattern of imipramine hydrochloride. In addition, the x-ray diffraction patterns of known forms of fumaric acid in the ICDD PFD-4 database (International Centre for Diffraction Data, 12 Campus Boulevard, Newtown Square, Pa. 19073-3273 U.S.A.) show that no fumaric acid peak occurs within 0.4 °2θ of 14.0 °2θ. Thus, the peak at about 14.0 °2θ characterizes the imipramine hydrochloride acid:fumaric acid cocrystal. No additional forms of fumaric acid were found other than the ones from the ICDD PFD-4 database.

Figure 18:
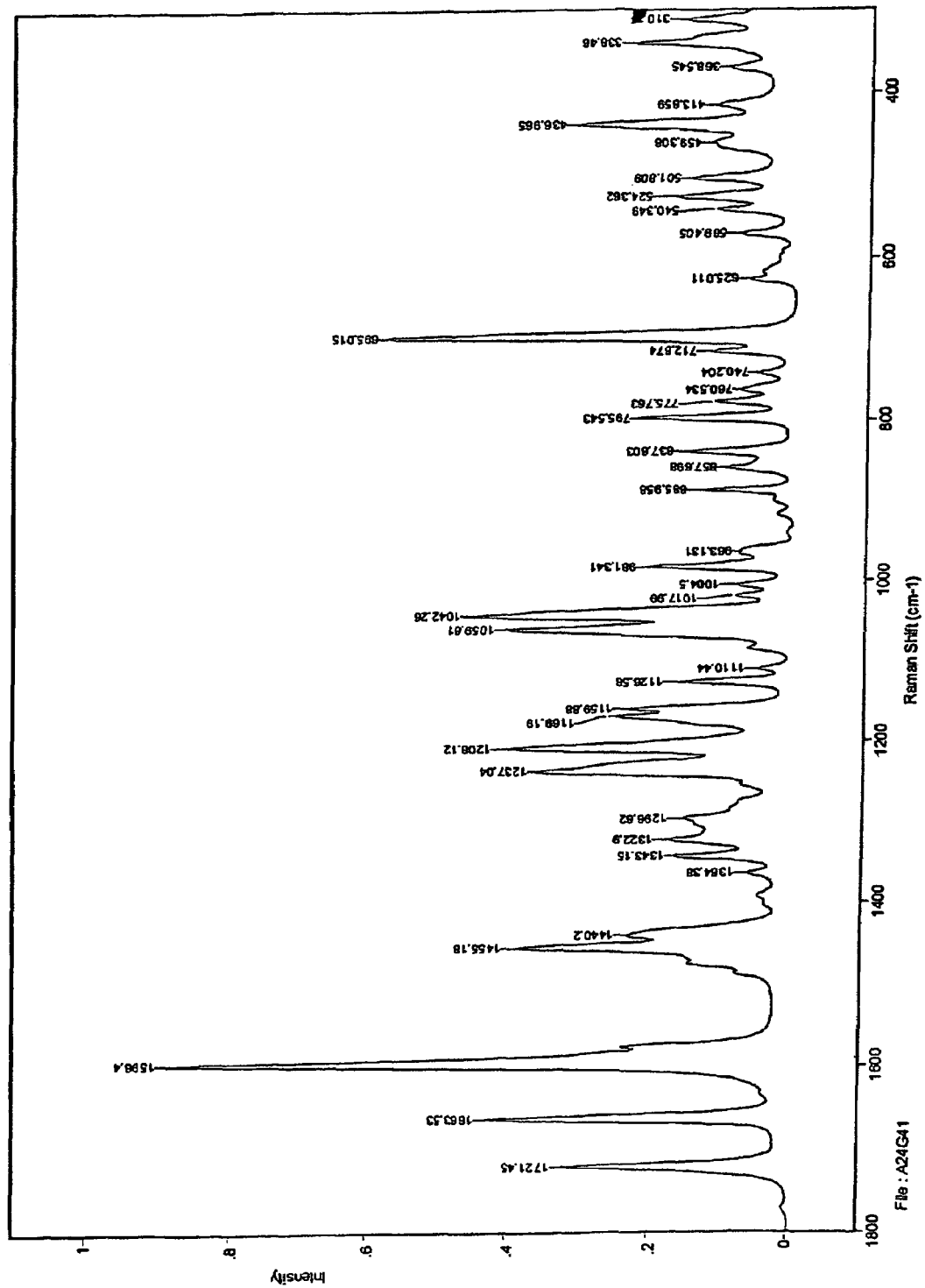
FIG. 18 is a Raman spectrum of a cocrystal of imipramine hydrochloride and fumaric acid.

FIG. 18 is a peak picked Raman spectrum of the cocrystal of imipramine hydrochloride and fumaric acid. While the entire Raman spectrum of FIG. 18 could be used to characterize the cocrystal of imipramine hydrochloride and fumaric acid, it is not necessary to use the entire spectrum. A subset of the spectrum may be used to characterize the cocrystal of imipramine hydrochloride and fumaric acid. For example, the peak at about 1721.5 cm$^{-1}$ is more than 4.0 cm$^{-1}$ away from Raman peaks in imipramine hydrochloride or fumaric acid alone. Thus, the peak at about 1721.5 cm$^{-1}$ may be used to characterize the cocrystal of imipramine hydrochloride and fumaric acid. Likewise, peaks at about 1663.5 cm$^{-1}$ and about 1455.2 cm$^{-1}$ are each more than 4.0 cm$^{-1}$ away from Raman peaks in imipramine hydrochloride and fumaric acid respectively. Raman spectra from imipramine hydrochloride and fumaric acid for comparison were collected on the starting materials prior to cocrystallization. Thus, the peaks at about 1663.5 cm$^{-1}$ and about 1455.2 cm$^{-1}$ may alone, together, or in combination with the peak at about 1721.5 cm$^{-1}$ be used to characterize the imipramine hydrochloride:fumaric acid cocrystal. The Raman data reported from FIG. 18 were all rounded to the nearest 0.1 cm$^{-1}$.

One may also use a combination of x-ray diffraction and Raman peaks to characterize a cocrystal. For example, any combination of the three Raman peaks at about 1721.5 cm$^{-1}$, about 1663.5 cm$^{-1}$, or about 1455.2 cm$^{-1}$ may be used with the x-ray peak at about 14.0 °2θ to characterize the imipramine hydrochloride:fumaric acid cocrystal. A dissolution study on the imipramine HCl:fumaric acid cocrystal indicated that the cocrystal dissolved at a rate of about 58% of imipramine HCl. This difference in dissolution rate may be used to develop a drug product comprising a cocrystal of imipramine HCl:fumaric acid to deliver a slower release dose profile of imipramine than imipramine HCl, as currently used.

Imipramine Hydrochloride:1-Hydroxy-2-Naphthoic Acid Cocrystal

Another cocrystal of the invention is a cocrystal of imipramine hydrochloride with 1-hydroxy-2-naphthoic acid. A single crystal x-ray showed the ratio of imipramine hydrochloride to 1-hydroxynaphthoic acid acid to be 1:1 in the unit cell.

Figure 19:
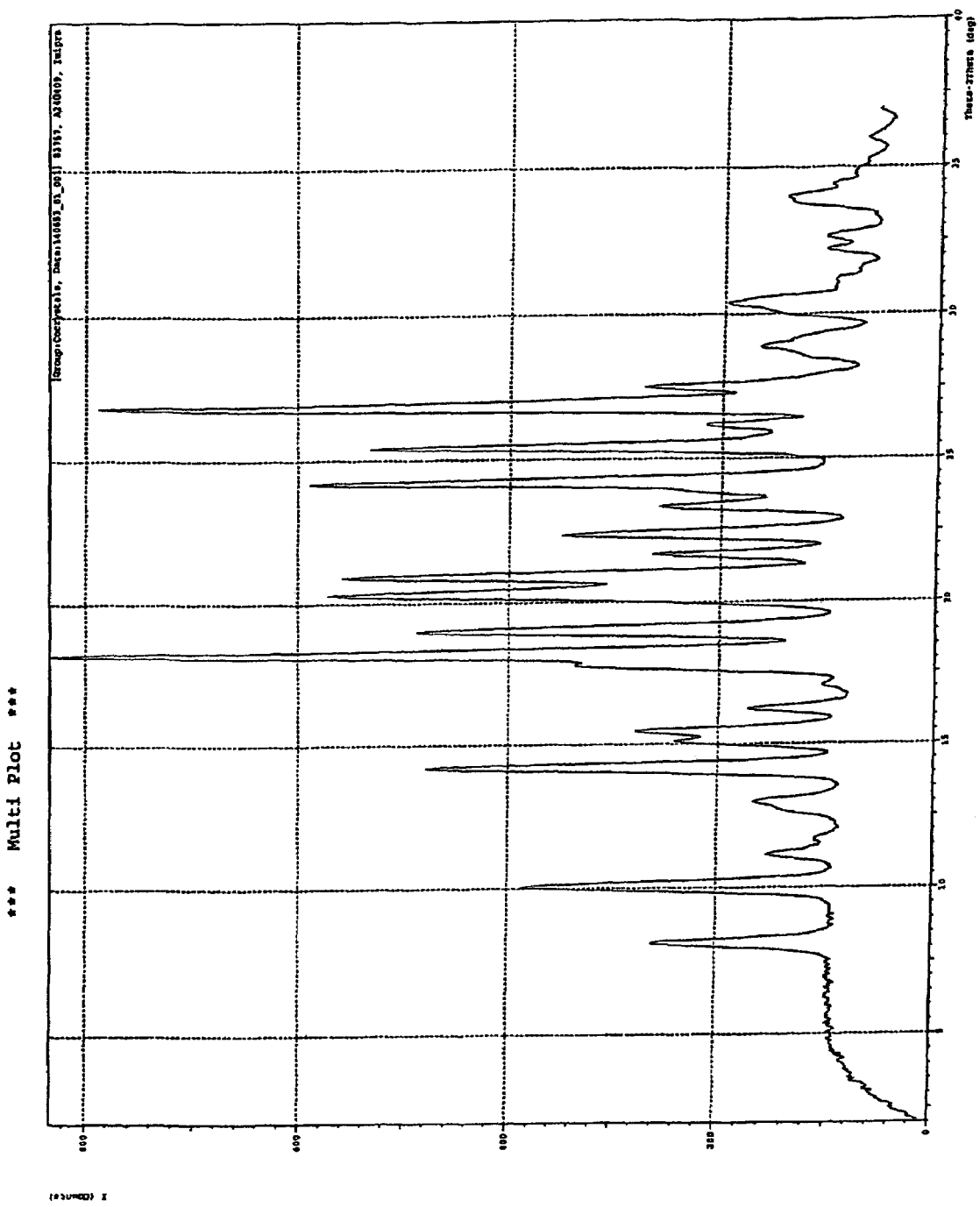
FIG. 19 is an x-ray powder diffraction pattern of a cocrystal of imipramine hydrochloride and 1-hydroxy-2-naphthoic acid.

FIG. 19 is a powder diffraction pattern of the imipramine hydrochloride:1-hydroxy-2-naphthoic acid cocrystal. FIG. 20 is the corresponding peak table for the diffractogram in FIG. 19. While the diffractogram of FIG. 19 could be used to characterize the cocrystal, it may also be characterized with a subset of that data. For example, the peak at about 8.1 °2θ in FIG. 19 is more than 0.4 °2θ away from any peak in the x-ray powder diffraction pattern of imipramine hydrochloride. In addition, the x-ray diffraction patterns of known forms of 1-hydroxy-2-naphthoic acid in the ICDD PFD-4 database (International Centre for Diffraction Data, 12 Campus Boulevard, Newtown Square, Pa. 19073-3273 U.S.A.) show that no 1-hydroxy-2-naphthoic acid peak occurs within 0.4 °2θ of 8.1 °2θ. Thus, the peak at about 8.1 °2θ characterizes the imipramine hydrochloride acid:1-hydroxy-2-naphthoic acid cocrystal. No additional forms of 1-hydroxy-2-naphthoic acid were found other than the ones from the ICDD PFD-4 database.

Figure 21:
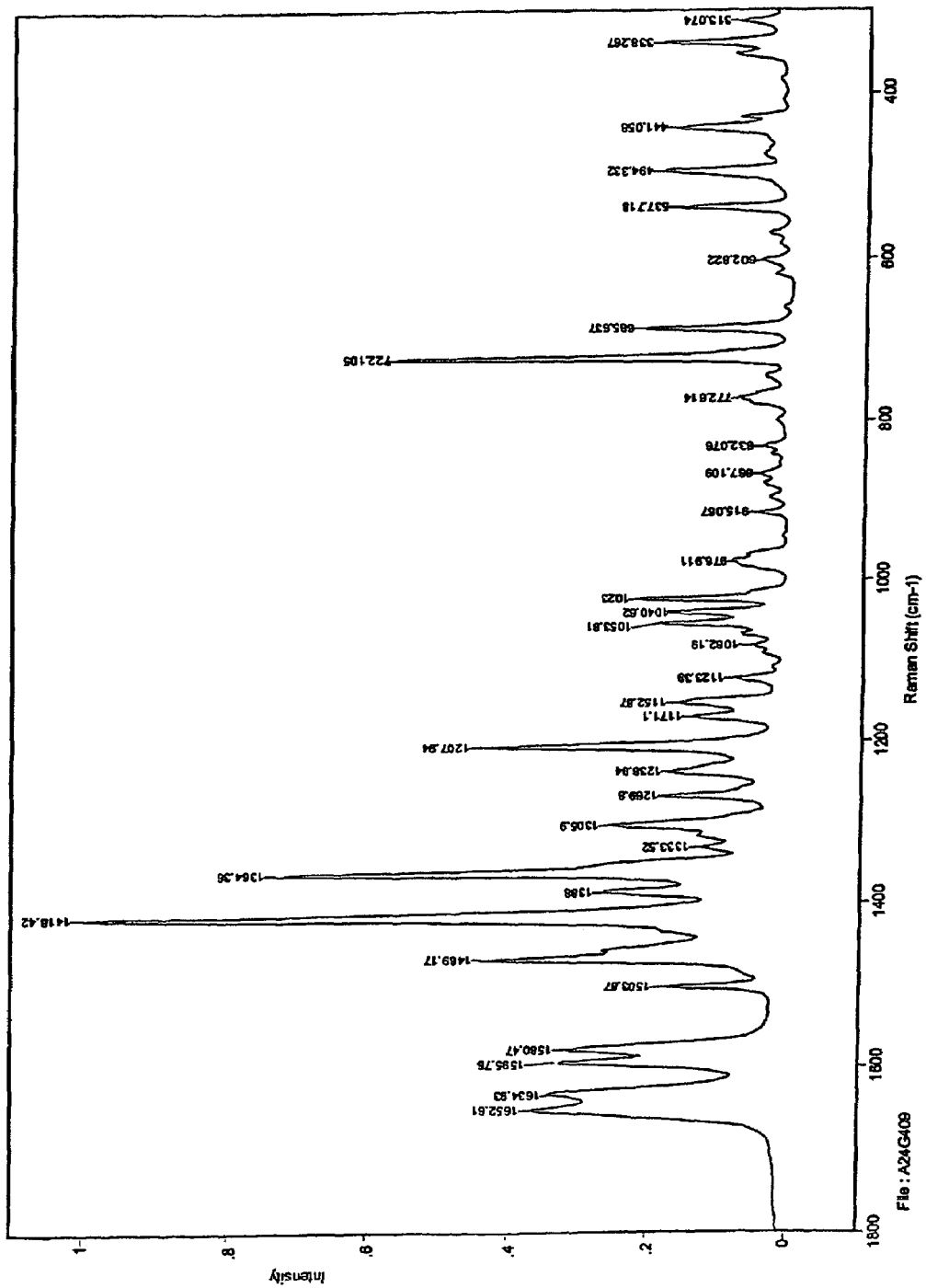
FIG. 21 is a Raman spectrum of a cocrystal of imipramine hydrochloride and 1-hydroxy-2-naphthoic acid.

FIG. 21 is a peak picked Raman spectrum of the cocrystal of imipramine hydrochloride and 1-hydroxy-2-naphthoic acid. While the entire Raman spectrum of FIG. 21 could be used to characterize the cocrystal of imipramine hydrochloride and 1-hydroxy-2-naphthoic acid, it is not necessary to use the entire spectrum. A subset of the spectrum may be used to characterize the cocrystal of imipramine hydrochloride and 1-hydroxy-2-naphthoic acid. For example, the peak at about 1652.6 cm$^{-1}$ is more than 4.0 cm$^{-1}$ away from Raman peaks in imipramine hydrochloride or 1-hydroxy-2-naphthoic acid alone. Thus, the peak at about 1652.6 cm$^{-1}$ may be used to characterize the cocrystal of imipramine hydrochloride and 1-hydroxy-2-naphthoic acid. Likewise, peaks at about 1364.4 cm$^{-1}$ and about 1305.9 cm$^{-1}$ are each more than 4.0 cm$^{-1}$ away from Raman peaks in imipramine hydrochloride and 1-hydroxy-2-naphthoic acid respectively. Raman spectra from imipramine hydrochloride and 1-hydroxy-2-naphthoic acid for comparison were collected on the starting materials prior to cocrystallization. Thus, the peaks at about 1364.4 cm$^{-1}$ and about 1305.9 cm$^{-1}$ may alone, together, or in combination with the peak at about 1652.6 cm$^{-1}$ be used to characterize the imipramine hydrochloride:1-hydroxy-2-naphthoic acid cocrystal. The Raman data reported from FIG. 21 were all rounded to the nearest 0.1 cm$^{-1}$.

One may also use a combination of x-ray diffraction and Raman peaks to characterize a cocrystal. For example, any combination of the three Raman peaks at about 1652.6 cm$^{-1}$, about 1364.4 cm$^{-1}$, or about 1305.9 cm$^{-1}$ may be used with the x-ray peak at about 8.1 °2θ to characterize the imipramine hydrochloride:1-hydroxy-2-naphthoic acid cocrystal.

A dissolution study on the imipramine HCl:1-hydroxy-2-naphthoic acid cocrystal indicated that the cocrystal dissolved at a much slower rate than that of imipramine HCl. The rate was found to be too slow to quantify accurately by the experiment conditions used. However, it was found that at 300 minutes, less than 0.0063 mg/mL of imipramine HCl had dissolved from the cocrystal, compared to 0.013 mg/mL of imipramine dissolved from imipramine HCl in two minutes. Thus, the cocrystal dissolved at a substantially slower rate than imipramine HCl.

Pharmaceutical Compositions

The invention relates to pharmaceutical compositions comprising a therapeutically effective amount of a cocrystal of the invention and a pharmaceutically acceptable carrier, (also known as a pharmaceutically acceptable excipient). As discussed above, metronidazole is used for the treatment of bacterial infections and imipramine hydrochloride is used for the treatment of depression. The cocrystals of the invention have the same pharmaceutical activity as their respective API. Pharmaceutical compositions for the treatment of those diseases and disorders contain a therapeutically effective amount of a cocrystal of the invention as appropriate for treatment of a patient with the particular disease or disorder.

A "therapeutically effective amount" of a cocrystal of the invention (discussed here concerning the pharmaceutical compositions refers to an amount sufficient to reduce the effects of an inflammatory or autoimmune response or disorder or sufficient to prevent, kill, or inhibit the growth of tumor cells. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; and the rate of excretion of a cocrystal of the invention; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J.Hardman and L. Limbird, eds., McGraw-Hill Press, 155-173, 2001, which is incorporated herein by reference.

A pharmaceutical composition of the invention may be any pharmaceutical form which maintains the crystalline form of a cocrystal of the invention. The pharmaceutical composition may be a solid form, a liquid suspension, an injectable composition, a topical form, or a transdermal form.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is one having a cocrystal of the invention, a carrier should be chosen that maintains the a cocrystal of the invention. In other words, the carrier should not substantially alter the crystalline form of the cocrystal of the invention, for example, a liquid carrier which would dissolve the cocrystal of the invention should not be used. Nor should the carrier be otherwise incompatible with a cocrystal of the invention, such as by producing any undesirable biological effect or otherwise interacting in a deleterious manner with any other component(s) of the pharmaceutical composition.

The pharmaceutical compositions of the invention are preferably formulated in unit dosage form for ease of administration and uniformity of dosage. A "unit dosage form" refers to a physically discrete unit of therapeutic agent appropriate for the patient to be treated. It will be understood, however, that the total daily dosage of a cocrystal of the invention and its pharmaceutical compositions according to the invention will be decided by the attending physician within the scope of sound medical judgment.

Because the crystalline form of a cocrystal of the invention is more easily maintained during their preparation, solid dosage forms are a preferred form for the pharmaceutical composition of the invention. Solid dosage forms for oral administration, which include capsules, tablets, pills, powders, and granules, are particularly preferred. In such solid dosage forms, the active compound is mixed with at least one inert, pharmaceutically acceptable carrier such as sodium citrate or dicalcium phosphate. The solid dosage form may also include one or more of: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar--agar, calcium carbonate, potato or tapioca starch, alginic acid, certain silicates, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate. The solid dosage forms may also comprise buffering agents. They may optionally contain opacifying agents and can also be of a composition that they release the active ingredient(s) only, or preferentially, in a certain part of the intestinal tract, optionally, in a delayed manner Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Solid dosage forms of pharmaceutical compositions of the invention can also be prepared with coatings and shells such as enteric coatings and other coatings well known in the pharmaceutical formulating art.

A cocrystal of the invention can be in a solid micro-encapsulated form with one or more carriers as discussed above. Microencapsulated forms of a cocrystal of the invention may also be used in soft and hard-filled gelatin capsules with carriers such as lactose or milk sugar as well as high molecular weight polyethylene glycols and the like.

The invention also provides methods for the treatment of the disorders discussed above. The cocrystals and pharmaceutical compositions containing them may, according to the invention, be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this invention can be administered to humans and other animals orally, rectally, parenterally, intravenously, intracisternally, intravaginally, intraperitoneally, topically (as by powders, ointments, or drops), bucally, as an oral or nasal spray, or the like, depending on the location and severity of the condition being treated. In certain embodiments, the cocrystals according to the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject.

EXAMPLES

Examples of further embodiments of the disclosure described herein are indicated below without, however, being limiting in nature.

FT-Raman spectra were acquired using two instruments. The first was an FT-Raman 960 spectrometer (ThermoElectron, Waltham, Mass.). This spectrometer uses an excitation wavelength of 1064 nm. Approximately 0.304 W of $Nd:YVO_4$ laser power was used to irradiate the sample. The Raman spectra were measured with a germanium (Ge) detector. The samples were prepared for analysis by placing the material in a glass capillary tube and positioning the capillary tube in a gold-coated capillary holder. A total of 1024 sample scans were collected from 98.2785 to 3600.4321 $cm^{-1}$ at a spectral resolution of 4.000 cm$^{-1}$, using Happ-Genzel apodization. Wavelength calibration was performed using sulfur and cyclohexane. The Raman spectra in FIGS. 5, 8, 15, 18, and 21 were collected on this instrument.

The second instrument used for Raman data was a Chromex Sentinel (Bruker Optics, Billerica, Mass.) dispersive Raman unit equipped with a 785 nm, 70 mW excitation laser and a TE cooled CCD (1024×256 pixels, <0.1e−/pixel/sec). A fiber-optically coupled filtering probe was used to collect data in a spectral range 300 cm$^{-1}$ to 1800 cm$^{-1}$ at a resolution of 4.000 cm$^{-1}$. Each spectrum is a result of six co-added 20 second scans. The unit has continuous automatic calibration using an internal standard. The data was collected by SentinelSoft (Bruker Optics, Billerica, Mass.) data acquisition.

All Raman spectra were processed in GRAMS/AI V.701 (ThermoElectron, Waltham, Mass.). A multi-point baseline correction was performed, for ease of comparison the spectra were normalized so that the highest peak in each spectra was set to a value of 1.0. The display was set to show data from 1800 to 300 cm$^{-1}$ regardless of the acquisition range. Peaks were displayed by choosing the default peak-picking parameters and then setting the peak separation parameter to 22, the threshold to 0.022 and the smoothing points to 6 with the exception of: the threshold value for imipramine hydrochloride:(+)-camphoric acid was set as 0.032 and the smoothing number for imipramine hydrochloride:fumaric acid was set to 4. Raman spectra for metronidazole, imipramine HCl, and guest compounds were obtained for reference purposes from Sigma-Aldrich (St. Louis, Mo.).

X-ray powder diffraction (XRPD) analyses were performed using a Bruker D-8 Discover diffractometer and Bruker's General Area Diffraction Detection System (GADDS, v.4.1.20) (Madison, Wis.). An incident beam of Cu Kα radiation was produced using a fine-focus tube (40 kV, 40 mA, age about 9 months), a properly-aligned Gobel Ni-C mirror (age about 9 months) and a 0.5 mm double-pinhole collimator. Each sample was packed between 3-micron thick Etnom™ films to form a portable disc-shaped specimen having a nominal thickness of 1 mm and a diameter of about 6 mm. Each prepared specimen was loaded in a holder secured to a translation stage and analyzed in transmission geometry. The incident beam was scanned and rastered to optimize orientation statistics. A beam-stop was used to minimize air scatter from the incident beam at low angles. Diffraction patterns were collected in 300 seconds using a Hi-Star (Bruker AXS) area detector located 15 cm from the sample and at an angle of 19.5° 2θ, and processed using GADDS. The intensity in the GADDS image of the diffraction pattern was integrated from 2 to 37° 2θ and from −163° to −17° chi, using bin normalized intensity, and a integration using a step size of 0.04° 2θ. The integrated patterns display diffraction intensity as a function of 2θ. Prior to the analyses a silicon standard was analyzed to verify the Si 111 peak position was within ±0.05° 2θ.

Instrument alignment was verified by measuring the 2θ positions of peaks from a sample of NIST SRM 676 (National Institute of Standards and Technology Standard Reference Material) alumina immediately prior to analyses of the cocrystal samples. A specimen of SRM 676 was prepared like the cocrystal powders and positioned in the same multi-sample holder containing the cocrystals (see below) at location X=14.789 mm, Y=27.880 mm, Z=−16.327 mm. The position of the diffraction peaks with hkls of 102, 104, 110, and 113 (25.6 to 43.4° 2θ) were within 0.05° 2θ of the positions calculated from the lattice parameters provided on the SRM 676 Certificate of Analysis.

Each specimen holder was held in a multi-sample holder which was attached to the XYZ stage of the Bruker D8. The incident beam was transmitted through the center of each specimen holder. The incident beam was scanned 20° 2θ and rastered in the YZ directions with amplitude of ±1 mm about the center of the specimen to optimize orientation statistics.

Each integrated data file was converted into a file format which could be read by Shimadzu XRD-6000 (Kyoto, Japan) software version 4.1 (for NT/98). Each file was imported into the Overlay module of the Shimadzu software and images of the diffraction patterns were generated. Each file was imported into the Basic Process module of the Shimadzu software and processed using the settings described in Table 2:

TABLE 2

Smoothing - off (No)
B.G.Subtraction - off (No)
Ka1-a2 - on (Manual; Ka1-a2 ratio = 50)
Peak - on (Manual; Differential Points = 9, FWHM threshold = 0.0500, FWHM Ratio = 2, Intensity Threshold = variable)
System Error Correction - off (No)
Precise Peak Correction - off (No)

The Ka1-a2 setting was used to electronically remove peaks arising from the Kα2 x-ray wavelength and retain only peaks arising from the Kα1 x-ray wavelength. The Peak module was used to generate a peak list from the data. The x-ray diffraction patterns generated appear in FIGS. 1, 6, 9, 16, and 19. The peak list data appear in FIGS. 2, 7, 14, 17, and 20. Unless otherwise specified, the experimental data for x-ray powder diffraction and Raman spectroscopy were collected at room temperature.

Example 1

Cocrystal Screen of Metronidazole

Cocrystals of metronidazole formed with carboxylic acid guests were identified by screening metronidazole against a set of 23 carboxylic guest acids. The screen was performed in a 96 well plate (Greiner 96-Well Plate—polypropylene, round U-bottom, chimney style). Each well contained 100 μl of Metronidazole in a 0.1 M solution of tetrahydrofuran (THF) (172.1 mg of metronidazole dissolved in 10.0 mL of tetrahydrofuran).

Carboxylic acid guest solutions were prepared by dissolving each one of the 23 carboxylic acid guests identified in table 1 separately in one of four solvent systems (1:1 (volume) THF:ethanol; 2:1:1 (volume) THF:propionitrile:t-butyl alcohol; 2:1:1 (volume) THF:MEK:TFE; or 1:1 (volume) THF:p-dioxane to form 0.1M stock solutions. Thus, a total of 92 different 0.1 M stock carboxylic acid guest solutions were prepared. The stock solutions were used to charge 92 wells of the 96 well plate. For the guest molecules containing one carboxylic acid group, 100 μl of each 0.1M stock solution were used to charge the wells of the well plate. For the guest molecules containing two carboxylic acid groups, 50 μl of each 0.1M stock solution were used to charge the wells of the well plate. The remaining four wells of the 96 well plate were used as controls and contained only metronidazole with each well containing 100 μl of the metronidazole stock solution plus 100 μl of one of the four different solvent systems used to make carboxylic acid guest solutions.

Each well of the well plate was sealed with a foil seal and one hole with an approximate diameter of 1 mm was punched in the foil over each well using a 200 μl polypropylene pipette tip. The plate was allowed to stand at room temperature and the solutions in the wells slowly evaporated. After three days the foil was removed and the resulting solids were examined by optical microscopy. Raman spectra were also collected from the solid samples in each well. By comparing the spectra collected from the solids in the wells of the well plate with (1) the Raman spectra taken on solids from wells containing only metronidazole and (2) Raman spectra of known forms of the guest acids, it was determined that two sets of cocrystals had formed, one with gallic acid and one with gentisic acid. Each of the four solution wells containing metronidazole:gallic acid compositions had crystallized as cocrystals. In addition, each of the four wells containing the metronidazole:gentisic acid compositions had crystallized as cocrystals.

Example 2

Scale Up of Metronidazole:Gentisic Acid 0.712 g of metronidazole were added to 4 mL of 2,2,2-trifluoroethanol (TFE) in a 20 mL vial. The suspension was stirred and warmed with a commercial heat gun on low power until the solids were dissolved. In a separate 20 mL vial, 0.642 g of gentisic acid (2,5-dihydroxybenzoic acid) were added to 4 mL of acetonitrile (ACN). The suspension was stirred and warmed with a commercial heat gun on low power until the solids were dissolved. The two solutions were filtered (0.2 micron filter) into the same clean 20 mL vial. The solution was seeded with a sample from the metronidazole:gentisic acid cocrystal from example 1 and the solution was allowed to cool to room temperature and stand for four hours. The product was isolated by filtration and air dried. Yield: 1.01 g (75%). X-ray powder diffraction data were collected and the results are reported in FIGS. 1 and 2. The Raman spectrum of this material is reported in FIG. 5.

Example 3

Scale Up of Metronidazole:Gallic Acid 0.315 g of metronidazole were added to 3 mL of trifluoroethanol (TFE) in a 20 mL vial. The suspension was stirred and warmed with a commercial heat gun on low power until the solids were dissolved 0.312 g of gallic acid were added to 2.5 mL of acetonitrile (ACN) in a 20 mL vial. The suspension was stirred and warmed with a commercial heat gun on low power until the solids were dissolved The two solutions were filtered (0.2 micron filter) into the same clean vial. The resulting solution was stored at 3 degrees C. overnight. A solid product formed and was isolated by filtration and air dried. Yield: 403 mg (64%). The formation of the metronidazole:gallic acid cocrystal of example 1 was confirmed by Raman spectroscopy. X-ray powder diffraction data were collected and the results are reported in FIGS. 6 and 7. A Raman spectrum is reported in FIG. 8

Example 4

Grinding Experiments

Grinding experiments were performed on both the gentisic acid and gallic acid cocrystals using a Retsch MM200 mixer mill and a 2.5 mL agate grinding vial. In one grinding experiment, 17.1 mg of metronidazole (0.1 mmol) was ground with 15.5 mg of gentisic acid (0.1 mmol). In another grinding experiment, 17.3 mg of metronidazole (0.1 mmol) was ground with 17.1 mg of gallic acid (0.1 mmol). Samples were processed at room temperature for between 5 and 8 minutes. The experiment was stopped once at approximately 3 to 4 minutes of processing time and the solid material on the sides of the agate vial was scraped off the walls with a spatula. The processing was then continued for an additional 2 to 4 minutes. The resulting material was recovered by scraping the solids off the walls of the agate vial with a metal spatula. The material was stored under ambient conditions. The material was characterized by Raman spectroscopy. Comparing spectra of the ground cocrystals with the results obtained from the well plates in example 1 indicated that the cocrystal was formed in the grinding experiments.

Example 5

Kofler Experiments with Imiprimine HCl and (+)-Camphoric Acid

Binary melt experiments using Kofler techniques were performed. Imiprimine HCl (imiprimine hydrochloride) was screened against the guest compounds of table 2. The Kofler techniques were used to test for potential cocrystallization of two molecular components. The Kofler techniques employed involved melting the two components individually on a microscope slide. A coverslip was applied to the slide, causing the melted components to merge with mixing occurring at the interface of the liquids. The interface region was observed for the formation of solids. When solids formed, they were analyzed to determine identity. Methyl benzoate was the high boiling liquid used in the Kofler experiments with imiprimine HCl.

The guest (+)-camphoric acid yielded a cocrystal in the amount of about 0.5 mg with imipramine HCl using the Kofler technique described above. A scaled up experiment was performed by dissolving millimolar quantities of a 1:1 ratio of 319 mg of imiprimine HCl and 201 mg of (+)-camphoric acid in hot acetonitrile, seeding with the cocrystal solid prepared in a Kofler experiment, cooling the solution in an ice bath for 45 minutes, and isolating the solid by filtration. The solid was characterized by Raman spectroscopy. FIGS. 9 and 14 are the x-ray diffraction pattern and corresponding peak lists for the cocrystal and FIG. 15 is the corresponding Raman spectrum.

Example 6

Cocrystals of Imipramine HCl Using Well Plates

Cocrystals of imipramine hydrochloride formed with carboxylic acid guests were identified by screening imiprimine HCl against a set of 23 carboxylic guest acids. The screen was performed in a 96 well plate (Greiner 96-Well Plate—polypropylene, round U-bottom, chimney style). Each well contained 100 µl of imiprimine HCl in a 0.1 M solution in ethanol (320.2 mg of imipramine HCl dissolved in 10.0 mL of ethanol).

Carboxylic acid guest solutions were prepared by dissolving each one of the 23 carboxylic acid guests of table 2 separately in one of four solvent systems (1:1 (volume) THF:ethanol; 2:1:1 (volume) THF:propionitrile:t-butyl alcohol; 2:1:1 (volume) THF:MEK:TFE; or 1:1 (volume) THF:p-dioxane to form 0.1M stock solutions. Thus, a total of 92 different 0.1 M stock carboxylic acid guest solutions were prepared. The stock solutions were used to charge 92 wells of the 96 well plate. For the guest molecules containing one carboxylic acid group, 100 µl of each 0.1M stock solution were used to charge the wells of the well plate. For the guest molecules containing two carboxylic acid groups, 50 µl of each 0.1M stock solution were used to charge the wells of the well plate. The remaining four wells of the 96 well plate were used as controls and contained only metronidazole with each well containing 100 µl of the metronidazole stock solution plus 100 µl of one of the four different solvent systems used to make carboxylic acid guest solutions.

Each well of the well plate was sealed with a foil seal and one hole with an approximate diameter of 1 mm was punched in the foil over each well using a 200 µl polypropylene pipette tip. The plate was allowed to stand at room temperature and the solutions in the wells slowly evaporated. After three days the foil was removed and the resulting solids were examined by optical microscopy. Raman spectra were also collected from the solid samples in each well. By comparing the spectra collected from the solids in the wells of the well plate with (1) the Raman spectra taken on solids from wells containing only metronidazole and (2) Raman spectra of known forms of the guest acids, it was determined that three sets of cocrystals had formed, one with (+) camphoric acid, one with fumaric acid, and one with 1-hydroxy-2-naphthoic acid. Each of the four solution wells containing imiprimine HCl:(+)-camphoric acid compositions had crystallized as cocrystals. Each of the four solution wells containing imiprimine HCl:fumaric acid compositions had crystallized as cocrystals. In addition, each of the four wells containing the imiprimine HCl:1-hydroxy-2-naphthoic acid compositions had crystallized as cocrystals.

Example 7

Scale Up of Imipramine HCl and Fumaric Acid Cocrystal 638 mg of imiprimine HCl (2 mmol) and 117 mg of fumaric acid (1 mmol) were added to 3 mL of methanol in a 20 mL vial. The suspension was stirred and warmed with a commercial heat gun on low power until the solids were dissolved. The solution was allowed to cool in an ice bath for 30 minutes. The solid product was isolated by filtration and air dried. Yield: 505 mg (67%). Raman spectra and x-ray powder diffractograms were collected. FIG. 16 is the x-ray diffraction pattern of the cocrystal. FIG. 17 is the corresponding peak list and FIG. 18 is the Raman spectrum of the cocrystal.

Example 8

Scale Up of Imipramine HCl and 1-hydroxy-2-naphthoic Acid Cocrystal 638 mg of imiprimine HCl (2 mmol) and 375 mg of 1-hydroxy-2-naphthoic acid (2 mmol) were added to 4 mL of methanol in a 20 mL vial. The suspension was stirred and warmed with a commercial heat gun on low power until the solids were dissolved. The solution was allowed to cool in an ice bath for 3 hours. The solid product was isolated by filtration and air dried. Yield: 305 mg (60%). Raman spectra and x-ray powder diffractograms were collected. The x-ray diffraction pattern is in FIG. 19 and the corresponding peak list is in FIG. 20. FIG. 21 is a Raman spectrum of the cocrystal.

Example 9

Grinding to Make Imipramine HCl Cocrystals

Grinding experiments were performed on the (+)-camphoric acid, fumaric acid, and 1-hydroxy-2-naphthoic acid cocrystal systems using a Retsch MM200 mixer mill and a 2.5 mL agate grinding vial. In each experiment, samples were processed at room temperature for between 5 and 8 minutes. The experiment was stopped once at approximately 3 to 4 minutes of processing time and the solid material stuck to the sides of the agate vial was scraped off the walls with a spatula. The processing was then continued for an additional 2 to 4 minutes. The resulting material was recovered by scraping the solids off the walls of the agate vial with a metal spatula. The material was stored under ambient conditions. The material was characterized by Raman spectroscopy. In one experiment, 2.1 mg of imiprimine HCl (0.1 mmol) and 20.1 mg of (+)-camphoric acid (0.1 mmol) were ground together according to the procedure above. Raman spectroscopy indicated that no cocrystal was formed. In a second experiment, 32.1 mg of imiprimine HCl (0.1 mmol) and 20.1 mg of (+)-camphoric acid (0.1 mmol) were ground together according to the procedure above. Raman spectroscopy indicated that no cocrystal was formed. In a third experiment, 31.5 mg of imiprimine HCl (0.1 mmol) and 5.8 mg of fumaric acid (0.05 mmol) were ground together according to the procedure above. Raman spectroscopy indicated that a cocrystal was formed and was identical to the fumaric acid cocrystal of example 6. In a fourth experiment, 32.2 mg of imiprimine HCl (0.1 mmol) and 19.1 mg of 1-hydroxy-2-naphthoic acid (0.1 mmol) were ground together according to the procedure above. Raman spectroscopy indicated that a cocrystal was formed and was identical to the 1-hydroxy-2-naphthoic acid cocrystal as example 8.

Example 10

Intrinsic Dissolution of Metronidazole:Gallic Acid

Samples of metronidazole and the metronidazole cocrystal were compressed at 1000 psi for approximately one minute. The samples were then analyzed using X-ray powder diffraction. For each sample, X-ray diffractograms from before and after compression were compared for consistency.

Dissolution experiments were performed using a VanKel VK7010 dissolution apparatus equipped with a VK750D heater/circulator. An intrinsic dissolution apparatus (Woods apparatus) with a sample surface area of 0.50 cm$^2$ was used. A dissolution medium of water was used at 37° C. Each experiment used 900 mL of medium, degassed by helium sparge. The Woods apparatus was rotated at 100 rpm for each experiment. The pellet remaining after the cocrystal dissolution analysis was analyzed by X-ray powder diffraction for consistency of XRPD pattern.

Metronidazole and the metronidazole:gallic acid cocrystal solutions were analyzed with a Cary 50 UV-VIS single-beam spectrophotometer without dilution at room temperature in a 1.000 cm quartz cuvette. Metronidazole and the cocrystal were analyzed at a wavelength of 318 nm. The detector was zeroed with a cuvette filled with dissolution medium prior to sample analysis. Wavelength calibration was performed using holmium oxide. The photometric accuracy was verified by measuring the intensity of the light at the detector when filters of known optical density were placed in the path of the beam.

Example 11

Intrinsic Dissolution of Imipramine HCl:Fumaric Acid Cocrystal

Samples of imipramine HCl and a cocrystal of imipramine HCl and fumaric acid were compressed at 1000 psi for approximately one minute. The samples were then analyzed using X-ray powder diffraction. For each sample, X-ray diffractograms from before after compression were compared for consistency of XRPD pattern.

Dissolution experiments were performed using a VanKel VK7010 dissolution apparatus equipped with a VK750D heater/circulator and VK810 peristaltic pump. An intrinsic dissolution apparatus (Woods apparatus) with a sample surface area of 0.50 cm$^2$ was used. Dissolution media used were 34 mM aqueous NaCl solution, water at 37° C., and water at ambient temperature. Each experiment used 900 mL of medium, degassed by helium sparge. The Woods apparatus was rotated at 100 rpm for each experiment. The pellet remaining after the cocrystal dissolution analysis was analyzed by X-ray powder diffraction for consistency of pattern.

Imipramine HCl and the imipramine HCl:fumaric acid cocrystal solutions were analyzed with a Cary 50 UV-VIS single-beam spectrophotometer without dilution at room temperature in a 1.000 cm quartz cuvette. Imipramine HCl and the cocrystal were analyzed at a wavelength of 278 nm. The detector was zeroed with a cuvette filled with dissolution medium prior to sample analysis. Wavelength calibration was performed using holmium oxide. The photometric accuracy was verified by measuring the intensity of the light at the detector when filters of known optical density were placed in the path of the beam.

Example 12

Intrinsic Dissolution of Imipramine HCl:1-hydroxy-2-naphthoic Acid

Samples of imipramine HCl and a cocrystal of imipramine HCl and 1-hydroxy-2-naphthoic acid were compressed at 1000 psi for approximately one minute. The samples were then analyzed using X-ray powder diffraction. For each sample, X-ray diffractograms from before after compression were compared for consistency of XRPD pattern.

Dissolution experiments were performed using a VanKel VK7010 dissolution apparatus equipped with a VK750D heater/circulator and VK810 peristaltic pump. An intrinsic dissolution apparatus (Woods apparatus) with a sample surface area of 0.50 cm$^2$ was used. Dissolution medium used water at 23° C. Each experiment used 900 mL of medium, degassed by helium sparge. The Woods apparatus was rotated at 100 rpm for each experiment. The pellet remaining after the cocrystal dissolution analysis was analyzed by X-ray powder diffraction for consistency of pattern.

Imipramine HCl and the imipramine HCl:1-hydroxy-2-naphthoic acid cocrystal solutions were analyzed with a Cary 50 UV-VIS single-beam spectrophotometer without dilution at room temperature in a 1.000 cm quartz cuvette. Imipramine HCl and the cocrystal were analyzed at a wavelength of 278 nm. The detector was zeroed with a cuvette filled with dissolution medium prior to sample analysis. Wavelength calibration was performed using holmium oxide. The photometric accuracy was verified by measuring the intensity of the light at the detector when filters of known optical density were placed in the path of the beam.

Example 13

Single Crystal X-Ray Structures

The single crystal structure of the metronidazole:gentisic acid cocrystal and the imipramine HCl:fumaric acid cocrystal were determined. Single crystals of the metronidazole gentisic acid cocrystal were grown by slow evaporation of a acetonitrile solution containing equimolar amounts of metronidazole and gentisic acid. Single crystals of the imipramine HCl fumaric acid were grown by slow evaporation of a methanol solution containing equimolar amounts of imipramine HCl and fumaric acid.

Suitable single crystals were coated with Paratone N oil, suspended in a small fiber loop and placed in a cooled nitrogen gas stream at 173 K on a Bruker D8 SMART 1000 CCD (Madison, Wis.) sealed tube diffractometer with graphite monochromated CuK$_\alpha$ (1.54178 Å) radiation. Data were measured using a series of combinations of phi and omega scans with 10 s frame exposures and 0.3° frame widths. Data collection, indexing and initial cell refinements were all carried out using SMART (SMART Version 5.625, 2002, Bruker AXS, Inc., Analytical X-ray Systems, Madison Wis.) software. Frame integration and final cell refinements were done using SAINT (SAINT Version 6.36A, 2002, Bruker AXS, Inc., Analytical X-ray Systems, Madison Wis.) software. The final cell parameters were determined from least-squares refinement on 2394 reflections. The SADABS (SADABS V2.08, 2003, University of Göttingen, Germany) program was used to carry out absorption corrections.

The structure was solved using Direct methods and difference Fourier techniques (SHELXTL, V6.12) (SHELXTL V6.12, 2002, Bruker AXS, Inc., Analytical X-ray Systems, Madison Wis.). All the hydrogen atoms were located in a difference Fourier map and were included in the final cycles of least squares with isotropic U$_{ij}$'s or as riding atoms; all non-hydrogen atoms were refined anisotropically. Scattering factors and anomalous dispersion corrections are taken from the *International Tables for X-ray Crystallography* (A. J. C. Wilson (ed), *International Tables for X-ray Crystallography*, Volume C. Kynoch, Academic Publishers, Dordrecht, 1992, Tables 6.1.1.4 (pp. 500-502) and 4.2.6.8 (pp. 219-222)). Structure solution, refinement, graphics and generation of publication materials were performed by using SHELXTL, V6.12 software.

Figure 22:
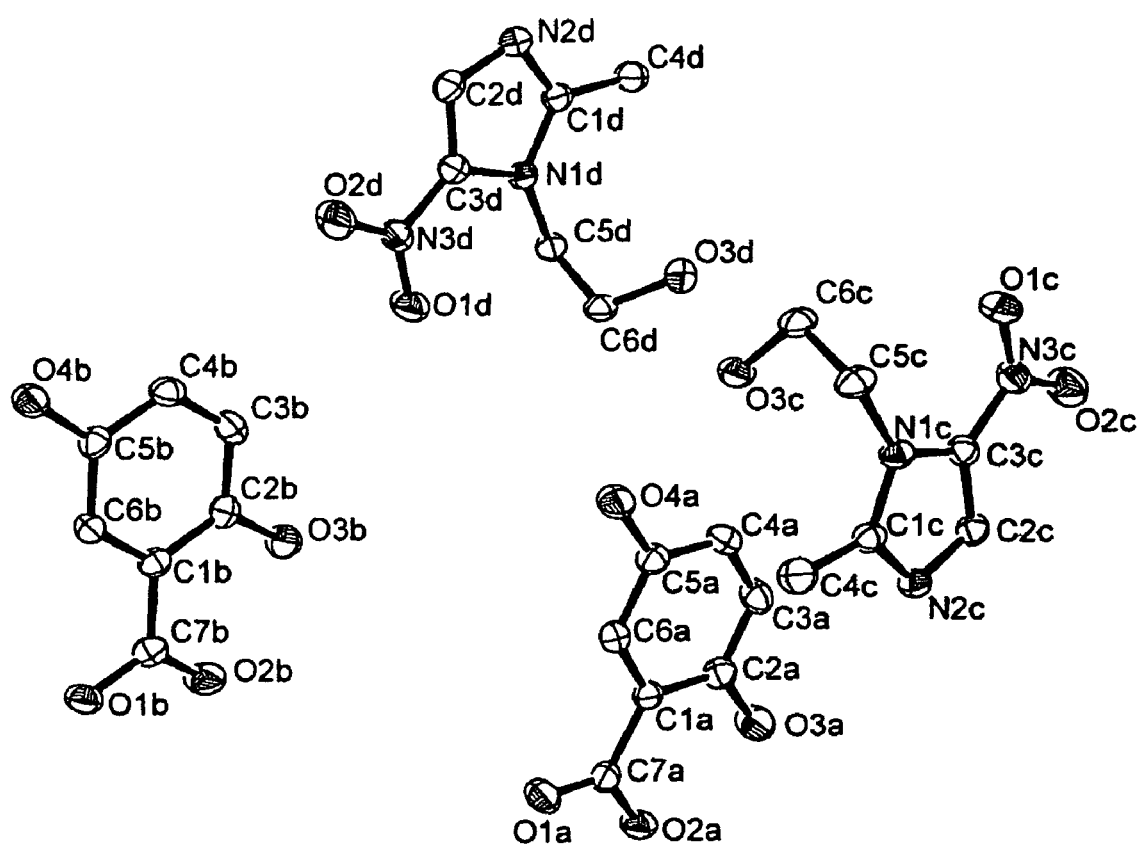
FIG. 22 is an ORTEP drawing of a single crystal structure of the metronidazole:gentisic acid cocrystal (ellipsoids are shown at 50% probability).

The acquisition and cell parameters that were determined for the metronidazole:gentisic acid cocrystal are shown in Table 3. The single crystal was collected at about 173 K. FIG. 22 is an ORTEP drawing of a single crystal structure of the metronidazole:gentisic acid cocrystal.

TABLE 3

| | | |
|---|---|---|
| Empirical formula | $C_{13}H_{15}N_3O_7$ | |
| Formula weight | 325.28 | |
| Temperature | 173(2) K | |
| Wavelength | 1.54178 Å | |
| Crystal system | Triclinic | |
| Space group | P-1 | |
| Unit cell dimensions | a = 8.3396(2) Å | α = 61.256(1)°. |
| | b = 14.1495(4) Å | β = 74.741(1)°. |
| | c = 14.2745(4) Å | γ = 86.833(2)°. |
| Volume | 1419.71(7) Å$^3$ | |
| Z | 4 | |
| Density (calculated) | 1.522 Mg/m$^3$ | |
| Absorption coefficient | 1.078 mm$^{-1}$ | |
| F(000) | 680 | |
| Crystal size | 0.57 × 0.33 × 0.25 mm$^3$ | |
| Theta range for data collection | 3.58 to 66.42°. | |
| Index ranges | −9 <= h <= 9, −16 <= k <= 14, −16 <= l <= 16 | |
| Reflections collected | 6972 | |
| Independent reflections | 4198 [R(int) = 0.0223] | |
| Completeness to theta = 66.42° | 84.4% | |
| Absorption correction | Semi-empirical from equivalents | |
| Max. and min. transmission | 1.00 and 0.864755 | |
| Refinement method | Full-matrix least-squares on F$^2$ | |
| Data/restraints/parameters | 4198/0/536 | |
| Goodness-of-fit on F$^2$ | 1.097 | |
| Final R indices [I > 2sigma(I)] | R1 = 0.0367, wR2 = 0.0964 | |
| R indices (all data) | R1 = 0.0409, wR2 = 0.0993 | |
| Extinction coefficient | 0.0018(3) | |
| Largest diff. peak and hole | 0.200 and −0.219 e.Å$^{-3}$ | |

Figure 23:
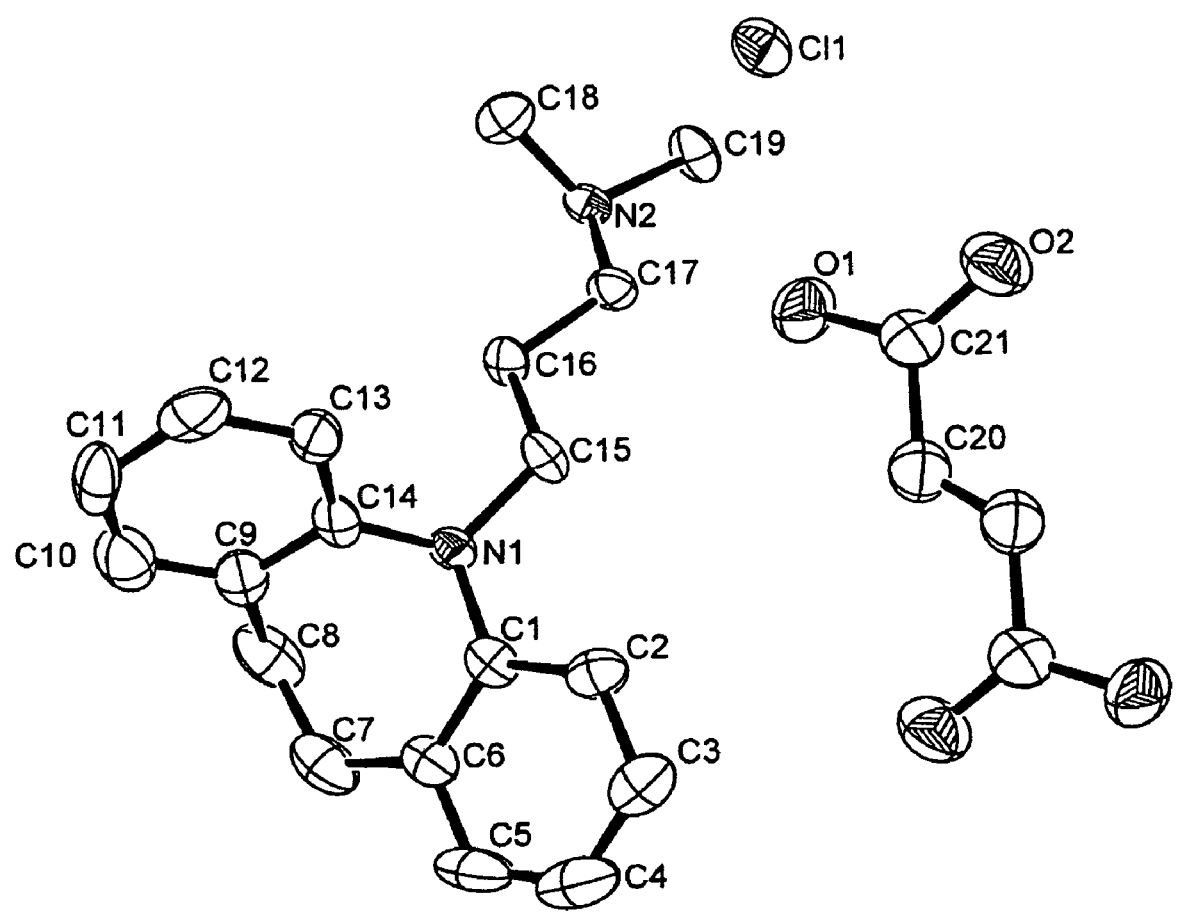
FIG. 23 is an ORTEP drawing of the single crystal structure of the imipramine HCl:fumaric acid cocrystal (ellipsoids are shown at 50% probability).

Table 4 contains the acquisition and cell parameters that were determined for the the imipramine HCl:fumaric acid cocrystal. The acquisition temperature was at about 173 K. FIG. 23 is an ORTEP drawing of the single crystal structure of the imipramine HCl:fumaric acid cocrystal.

TABLE 4

| | | |
|---|---|---|
| Empirical formula | C21 H27 Cl N2 O2 | |
| Formula weight | 374.90 | |
| Temperature | 173(2) K | |
| Wavelength | 1.54178 Å | |
| Crystal system | Monoclinic | |
| Space group | P2(1)/c | |
| Unit cell dimensions | a = 10.1690(16) Å | α = 90°. |
| | b = 7.1103(11) Å | β = 99.312(7)°. |
| | c = 27.947(5) Å | γ = 90°. |
| Volume | 1994.0(6) Å$^3$ | |
| Z | 4 | |
| Density (calculated) | 1.249 Mg/m$^3$ | |
| Absorption coefficient | 1.825 mm$^{-1}$ | |
| F(000) | 800 | |
| Crystal size | 0.36 × 0.15 × 0.13 mm$^3$ | |
| Theta range for data collection | 3.20 to 66.00°. | |
| Index ranges | −12 <= h <= 8, −5 <= k <= 7, −29 <= l <= 27 | |
| Reflections collected | 6058 | |
| Independent reflections | 2603 [R(int) = 0.0449] | |
| Completeness to theta = 66.00°, | 74.8% | |
| Absorption correction | Semi-empirical from equivalents | |
| Max. and min. transmission | 0.7973 and 0.5595 | |
| Refinement method | Full-matrix least-squares on F$^2$ | |
| Data/restraints/parameters | 2603/0/238 | |
| Goodness-of-fit on F$^2$ | 1.290 | |
| Final R indices [I > 2sigma(I)] | R1 = 0.0793, wR2 = 0.2200 | |
| R indices (all data) | R1 = 0.1189, wR2 = 0.2346 | |
| Extinction coefficient | 0.0017(4) | |
| Largest diff. peak and hole | 0.347 and −0.319 e.Å$^{-3}$ | |

Figure 24:
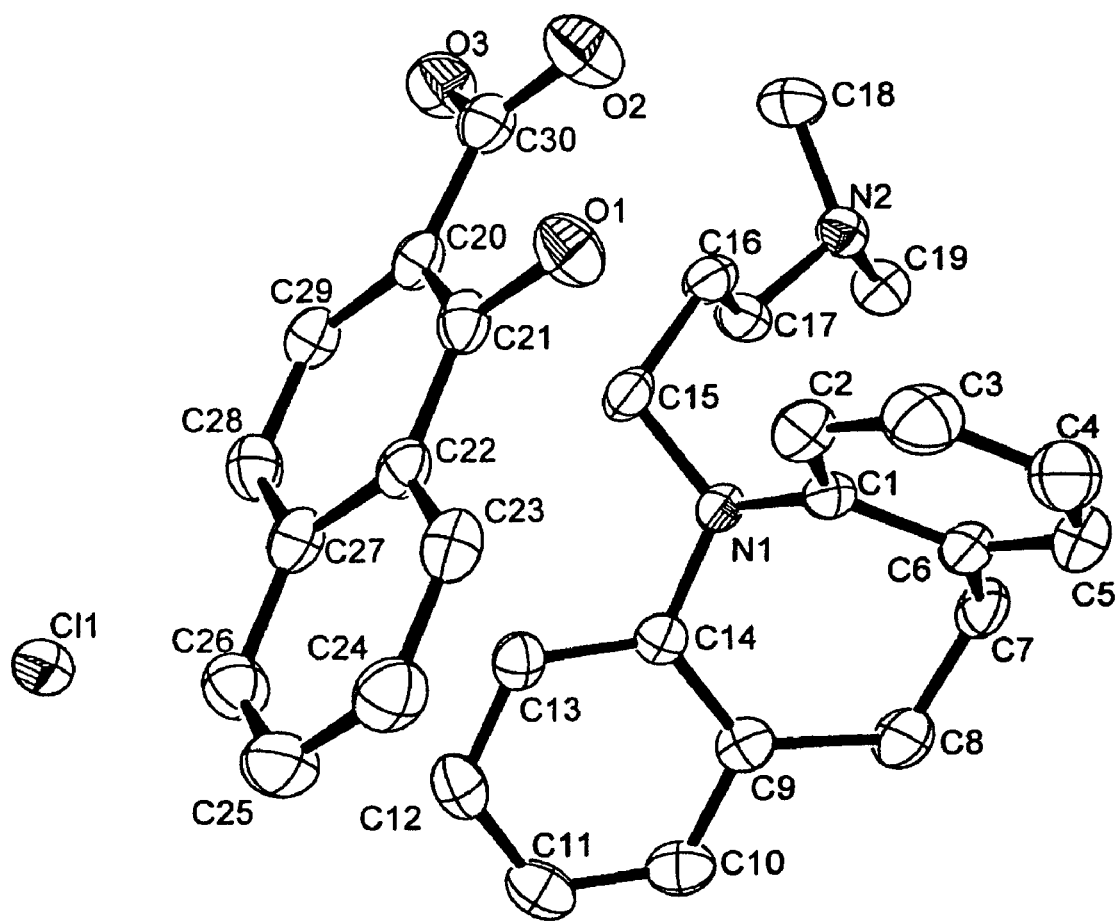
FIG. 24 is an ORTEP drawing of the single crystal structure of the imipramine HCl:1-hydroxy-2-naphthoic acid cocrystal (ellipsoids are shown at 50% probability).

Table 5 contains the acquisition and cell parameters that were determined for the the imipramine HCl:1-hydroxy-2-naphthoic acid cocrystal. The acquisition temperature was at about 173 K. FIG. 24 is an ORTEP drawing of the single crystal structure of the the imipramine HCl:1-hydroxy-2-naphthoic acid cocrystal.

TABLE 5

| | |
|---|---|
| Empirical formula | C30 H33 Cl N2 O3 |
| Formula weight | 505.03 |
| Temperature | 173(2) K |
| Wavelength | 1.54178 Å |
| Crystal system | Monoclinic |
| Space group | P2(1)/n |
| Unit cell dimensions | a = 11.0831(9) Å    a = 90°. |
| | b = 15.1038(11) Å   b = 93.530(3)°. |
| | c = 15.6570(14) Å   g = 90°. |
| Volume | 2616.0(4) Å3 |
| Z | 4 |
| Density (calculated) | 1.282 Mg/m3 |
| Absorption coefficient | 1.562 mm − 1 |
| F(000) | 1072 |
| Crystal size | 0.42 × 0.36 × 0.20 mm3 |
| Theta range for data collection | 4.07 to 66.32°. |
| Index ranges | −13 <= h <= 12, −17 <= k <= 17, −18 <= l <= 17 |
| Reflections collected | 18530 |
| Independent reflections | 4309 [R(int) = 0.0242] |
| Completeness to theta = 66.32° | 93.7% |
| Absorption correction | Semi-empirical from equivalents |
| Max. and min. transmission | 0.7452 and 0.5599 |
| Refinement method | Full-matrix least-squares on F2 |
| Data/restraints/parameters | 4309/0/329 |
| Goodness-of-fit on F2 | 1.061 |
| Final R indices [I > 2sigma(I)] | R1 = 0.0327, wR2 = 0.0831 |
| R indices (all data) | R1 = 0.0337, wR2 = 0.0838 |
| Largest diff. peak and hole | 0.258 and −0.226 e.Å − 3 |

I claim:

1. A cocrystal of metronidazole and gentisic acid having about a 1:1 molar ratio of metronidazole to gentisic acid in the unit cell and an x-ray diffracton peak at about 14.5 °2θ.

2. The cocrystal of metronidazole and gentisic acid of claim 1 having substantially the same x-ray diffraction pattern as FIG. 1.

3. A cocrystal of metronidazole and gentisic acid having about a 1:1 molar ratio of metronidazole to gentisic acid in the unit cell and a Raman peak at about 1189.7 cm$^{-1}$.

4. The cocrystal metronidazole and gentisic acid of claim 3 having a Raman spectrum substantially the same as FIG. 5.

5. A cocrystal of metronidazole and gallic acid having about a 1:1 molar ratio of metronidazole to gallic acid in the unit cell and an x-ray powder diffraction peak at about 15.2 °2θ.

6. The cocrystal of metronidazole and gallic acid of claim 5 having an x-ray powder diffraction pattern that is substantially the same as FIG. 6.

7. A cocrystal of metronidazole and gallic acid having about a 1:1 molar ratio of metronidazole to gallic acid in the unit cell and a Raman peak at 1493.5 cm$^{-1}$.

8. The cocrystal of metronidazole and gallic acid of claim 7 having a Raman spectrum substantially the same as that of FIG. 8.

9. A cocrystal of imipramine hydrochloride and (+)-camphoric acid having about a 1:1 molar ratio of imipramine hydrochloride to (+)-camphoric acid in the unit cell and an x-ray powder diffraction peak at about 5.4 °2θ.

10. The cocrystal of imipramine hydrochloride and (+)-camphoric add of claim 9 having substantially the same x-ray powder diffraction pattern of FIG. 9.

11. A cocrystal of imipramine hydrochloride and (+)-camphoric add having about a 1:1 molar ratio of imipramine hydrochloride to (+)-camphoric acid in the unit cell and a Raman peak at about 1059.1 cm$^{-1}$.

12. The cocrystal of imipramine hydrochloride and (+)-camphoric acid of claim 11 having a Raman spectrum substantially the same as that of FIG. 15.

13. A pharmaceutical composition comprising a 1:1 cocrystal of metronidazole and gentisic acid having an x-ray diffraction peak at about 14.5 °2θ and one or more pharmaceutically acceptable carrier.

14. A pharmaceutical composition comprising a 1:1 cocrystal of metronidazole and gallic acid having an x-ray powder diffraction peak at about 15.2 °2θ and one or more pharmaceutically acceptable carrier.

15. A pharmaceutical composition comprising a 1:1 cocrystal of imipramine hydrochloride and (+)-camphoric acid having an x-ray powder diffraction peak at about 5.4 °2θ and one or more pharmaceutically acceptable carrier.

* * * * *